United States Patent
Reasoner et al.

(10) Patent No.: US 10,420,865 B2
(45) Date of Patent: Sep. 24, 2019

(54) MEDICAL/SURGICAL WASTE COLLECTION UNIT WITH A LIGHT ASSEMBLY SEPARATE FROM THE PRIMARY DISPLAY, THE LIGHT ASSEMBLY PRESENTING INFORMATION ABOUT THE OPERATION OF THE SYSTEM BY SELECTIVELY OUTPUTTING LIGHT

(71) Applicant: Stryker Corporation, Kalamazoo, MI (US)

(72) Inventors: Stephen J. Reasoner, Kalamazoo, MI (US); Robert W. Childers, Portage, MI (US); Chamara Gamhewage, Kalamazoo, MI (US); Michael W. Hall, Mattawan, MI (US); Nathan K. Hogan, Portage, MI (US); Brian J. MacLachlan, Spring Lake, MI (US); Michael J. Miller, Kalamazoo, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 0 days.

(21) Appl. No.: 15/252,424

(22) Filed: Aug. 31, 2016

(65) Prior Publication Data
US 2016/0367732 A1 Dec. 22, 2016

Related U.S. Application Data

(63) Continuation of application No. PCT/US2015/018968, filed on Mar. 5, 2015.
(Continued)

(51) Int. Cl.
*A61M 1/00* (2006.01)

(52) U.S. Cl.
CPC ........ *A61M 1/0027* (2014.02); *A61M 1/0001* (2013.01); *A61M 1/0086* (2014.02);
(Continued)

(58) Field of Classification Search
CPC .............. A61M 1/0001; A61M 1/0027; A61M 1/0086; A61M 2205/3389;
(Continued)

(56) References Cited

U.S. PATENT DOCUMENTS

| 4,971,034 A | 11/1990 | Doi et al. |
| 5,554,049 A * | 9/1996 | Reynolds ........... H01R 13/6658 439/490 |

(Continued)

FOREIGN PATENT DOCUMENTS

| CN | 201076498 Y | 6/2008 |
| WO | 2007103842 A2 | 9/2007 |
| WO | 2013090579 A1 | 6/2013 |

OTHER PUBLICATIONS

EPO, "ISA Search Report and Written Opinion for PCT App. No. PCT/US2015/018968", dated Mar. 8, 2016.

*Primary Examiner* — Adam Marcetich
(74) *Attorney, Agent, or Firm* — Howard & Howard Attorneys PLLC

(57) ABSTRACT

A waste collection unit (40) with a primary display (106) on which information about the operation of the unit is presented. In addition to the primary display there is a light assembly (662) adjacent the fitting (614) to which a suction line is attached. The light assembly emits light of selectively colors or in a selected pattern based on an operation state of the waste collection unit.

15 Claims, 34 Drawing Sheets

Related U.S. Application Data

(60) Provisional application No. 61/948,772, filed on Mar. 6, 2014.

(52) U.S. Cl.
CPC .............. *A61M 2205/3389* (2013.01); *A61M 2205/502* (2013.01); *A61M 2205/584* (2013.01); *A61M 2205/587* (2013.01); *A61M 2209/084* (2013.01)

(58) Field of Classification Search
CPC ...... A61M 2205/502; A61M 2205/584; A61M 2205/587; A61M 2209/084
See application file for complete search history.

(56) References Cited

U.S. PATENT DOCUMENTS

| | | | |
|---|---|---|---|
| 5,997,733 A | 12/1999 | Wilbur et al. | |
| 6,068,627 A * | 5/2000 | Orszulak | A61B 18/12 606/34 |
| 6,109,760 A * | 8/2000 | Salatrik | B60N 3/14 219/200 |
| 6,331,246 B1 | 12/2001 | Beckham et al. | |
| 6,663,386 B1 * | 12/2003 | Moelsgaard | A61C 1/0046 433/215 |
| 6,902,673 B2 | 6/2005 | Smit et al. | |
| 7,497,340 B2 | 3/2009 | Hershberger et al. | |
| 7,615,037 B2 | 11/2009 | Murray et al. | |
| 7,621,898 B2 | 11/2009 | Lalomia et al. | |
| 7,872,746 B2 | 1/2011 | Gao et al. | |
| 8,294,586 B2 | 10/2012 | Pidgeon et al. | |
| 8,409,170 B2 | 4/2013 | Locke et al. | |
| 9,138,515 B2 | 9/2015 | Locke et al. | |
| 10,016,538 B2 | 7/2018 | Locke et al. | |
| 10,105,470 B2 | 10/2018 | Reasoner et al. | |
| 2003/0054698 A1 * | 3/2003 | Lin | H01R 13/7172 439/668 |
| 2003/0164600 A1 | 9/2003 | Dunn et al. | |
| 2005/0139532 A1 | 6/2005 | Hershberger et al. | |
| 2005/0187529 A1 | 8/2005 | Reasoner et al. | |
| 2005/0266723 A1 * | 12/2005 | Graham | H01R 13/6641 439/490 |
| 2006/0096057 A1 * | 5/2006 | Chatfield | A47L 9/02 15/324 |
| 2007/0135778 A1 * | 6/2007 | Murray | A61M 1/0001 604/317 |
| 2007/0135779 A1 * | 6/2007 | Lalomia | A61M 1/0005 604/319 |
| 2008/0166914 A1 * | 7/2008 | Buzil | H01R 13/70 439/490 |
| 2008/0262442 A1 * | 10/2008 | Carlin | A61B 5/1076 604/264 |
| 2009/0054890 A1 * | 2/2009 | DeCarlo | A61B 18/1402 606/34 |
| 2009/0280677 A1 * | 11/2009 | Gingrich, III | H01R 13/7172 439/490 |
| 2010/0068918 A1 * | 3/2010 | Houir Alamii | H01R 13/641 439/490 |
| 2010/0240246 A1 * | 9/2010 | Williams | H01R 13/717 439/490 |
| 2011/0184244 A1 * | 7/2011 | Kagaya | A61B 1/00117 600/182 |
| 2012/0035425 A1 * | 2/2012 | Schaller | A61F 9/00736 600/249 |
| 2013/0144227 A1 | 6/2013 | Locke et al. | |
| 2014/0257046 A1 * | 9/2014 | Steven | A61B 19/44 600/301 |
| 2015/0282985 A1 | 10/2015 | Ross et al. | |
| 2016/0331876 A1 | 11/2016 | Smith et al. | |

* cited by examiner

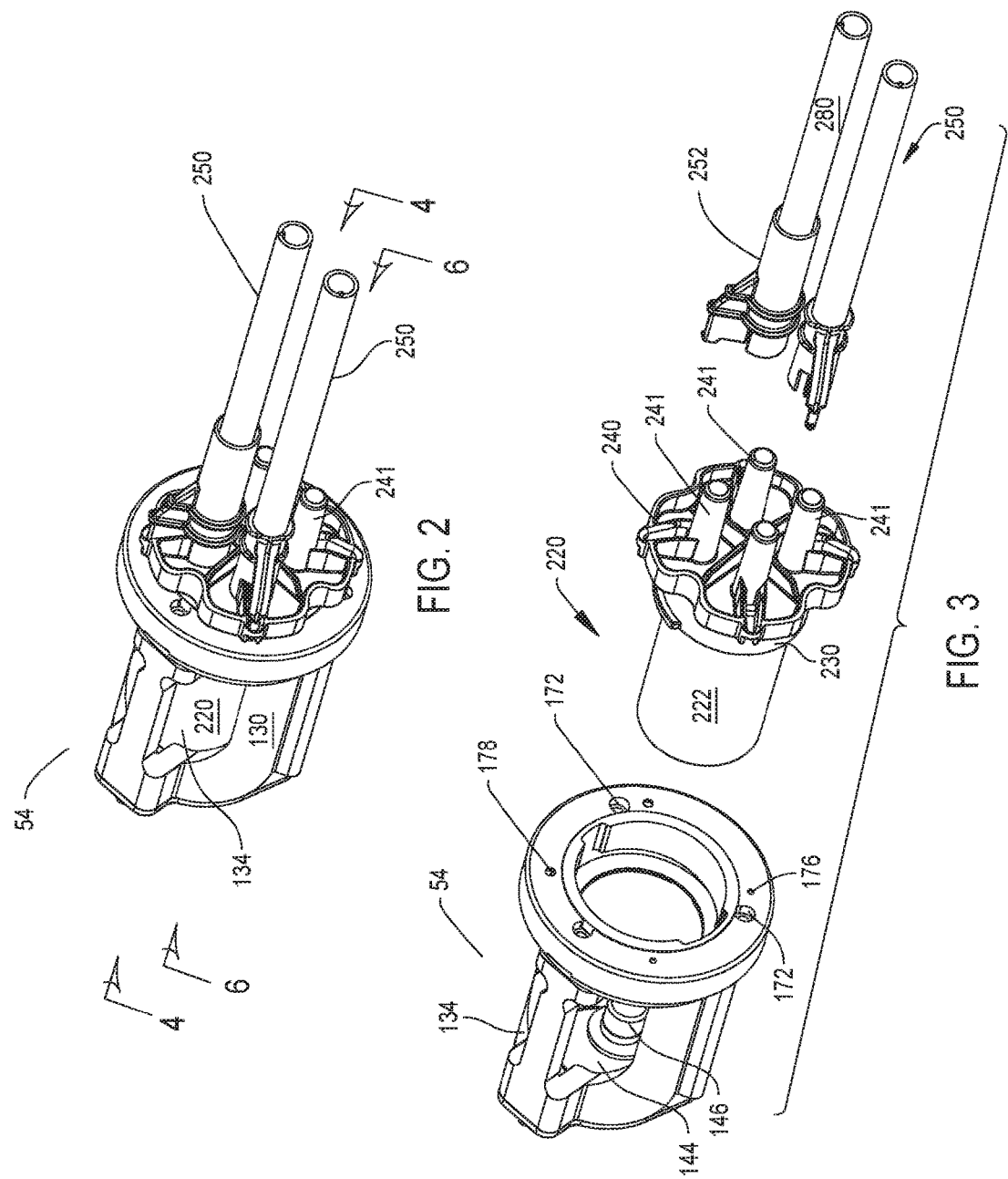

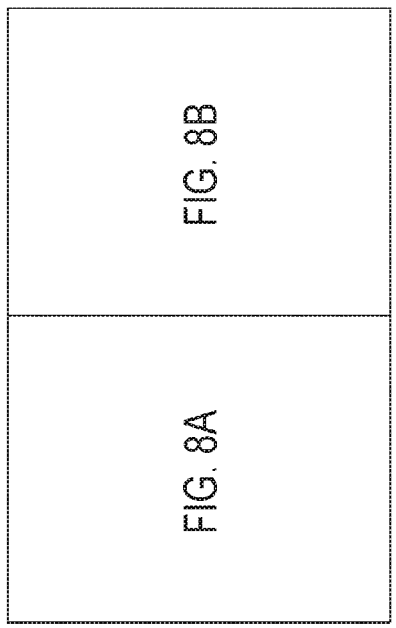
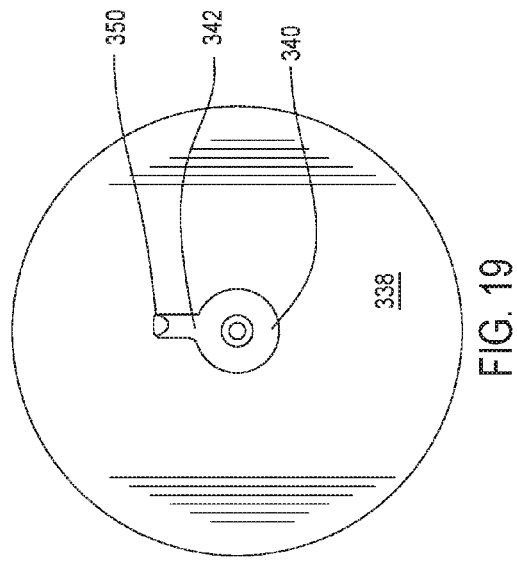

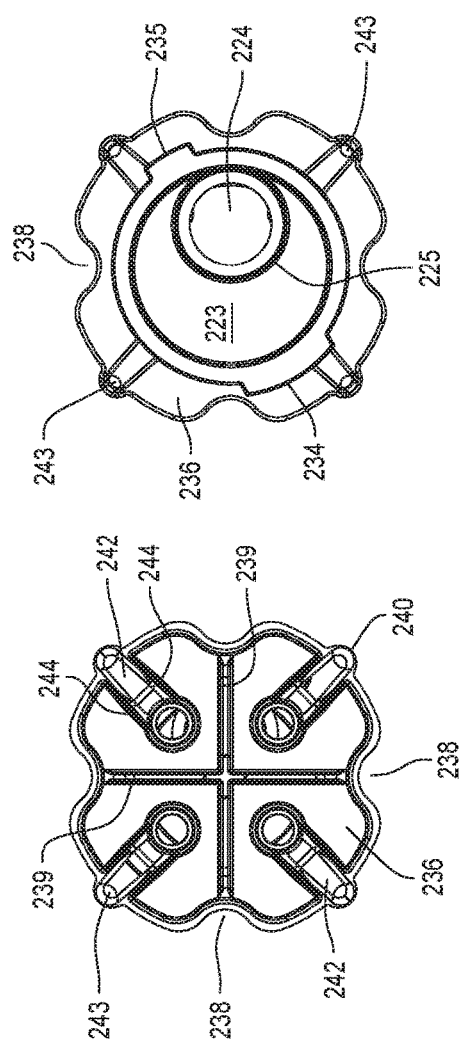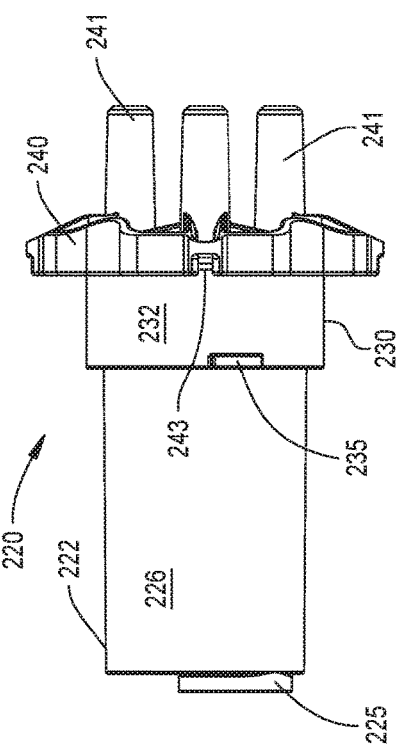

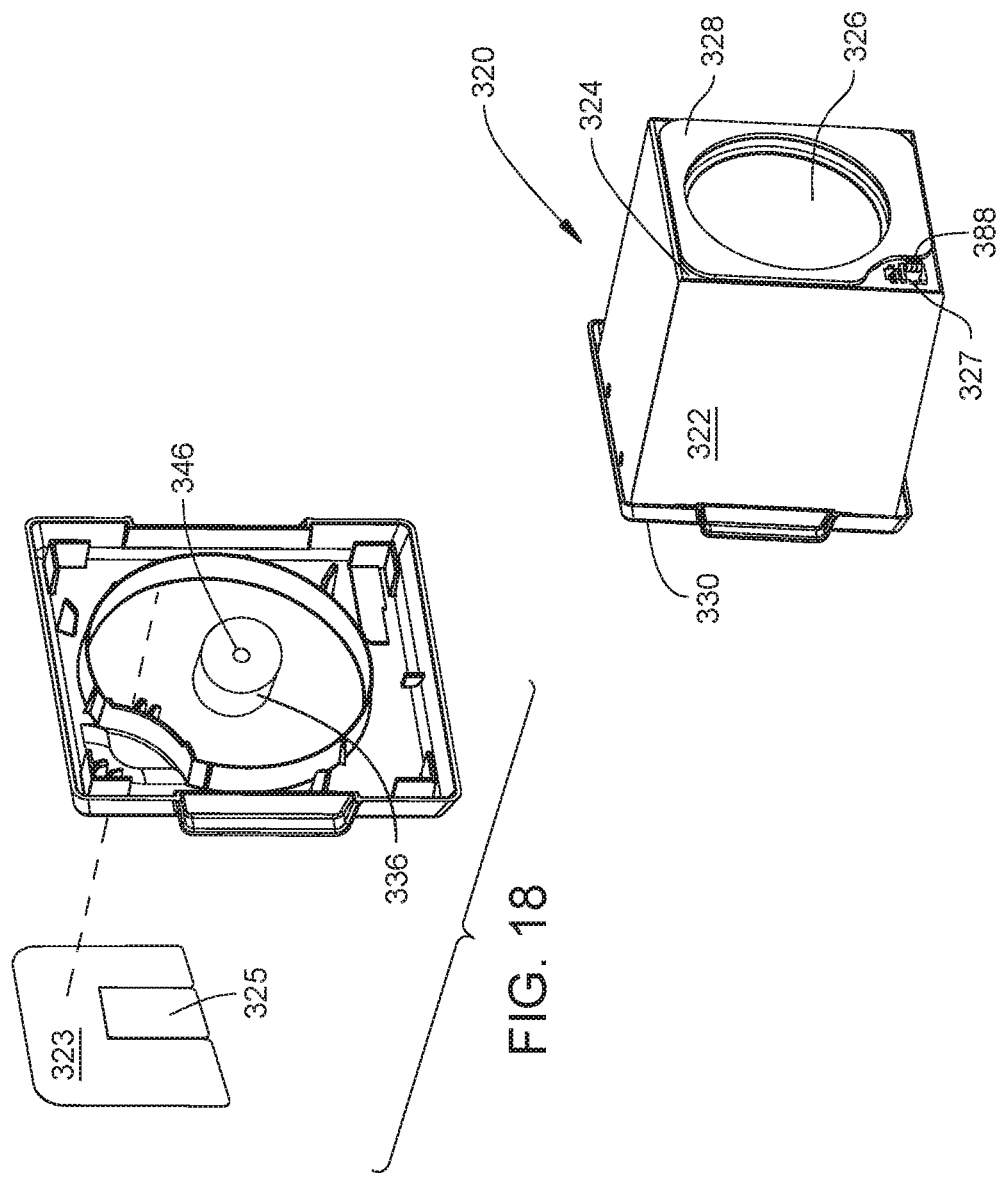

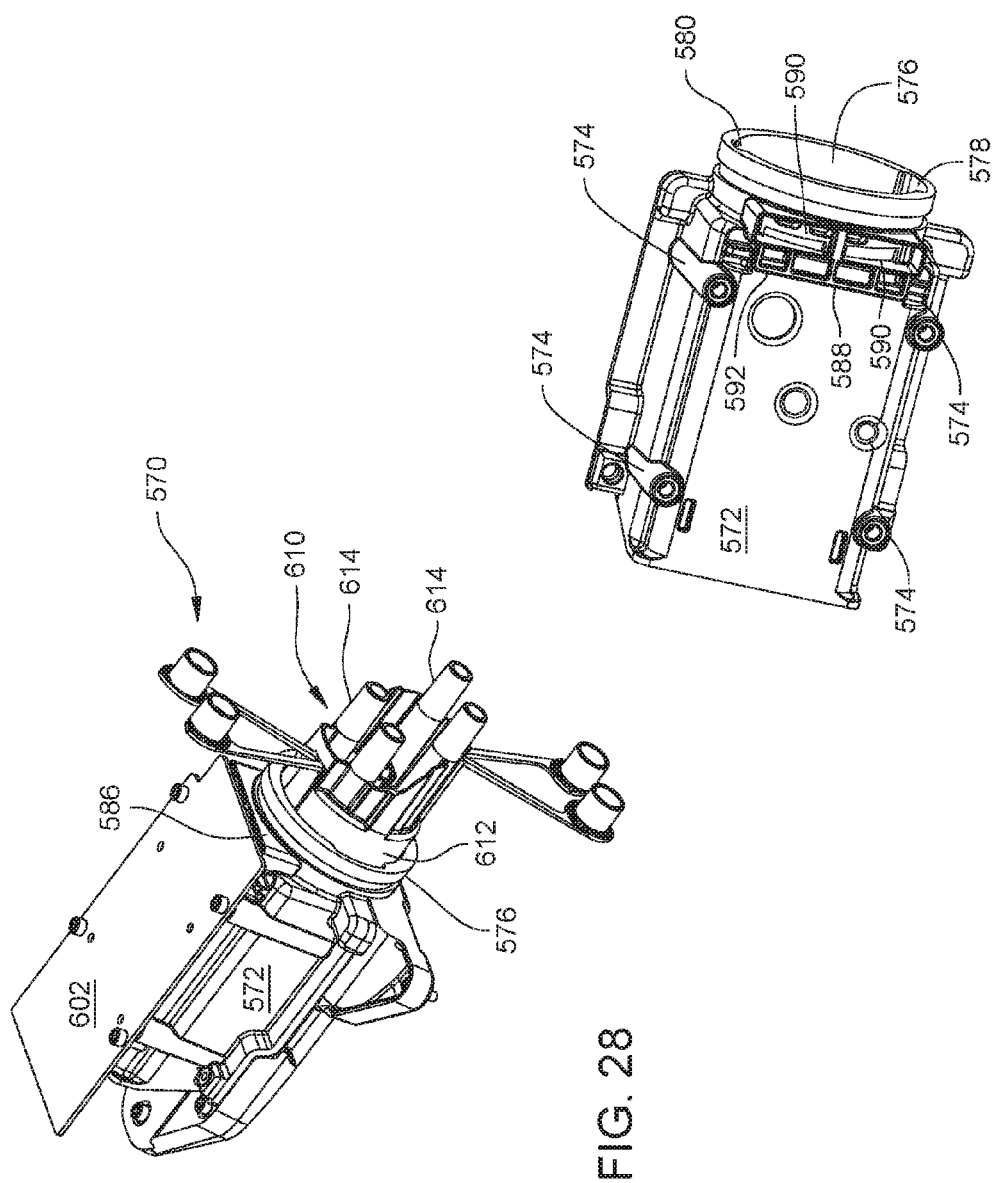

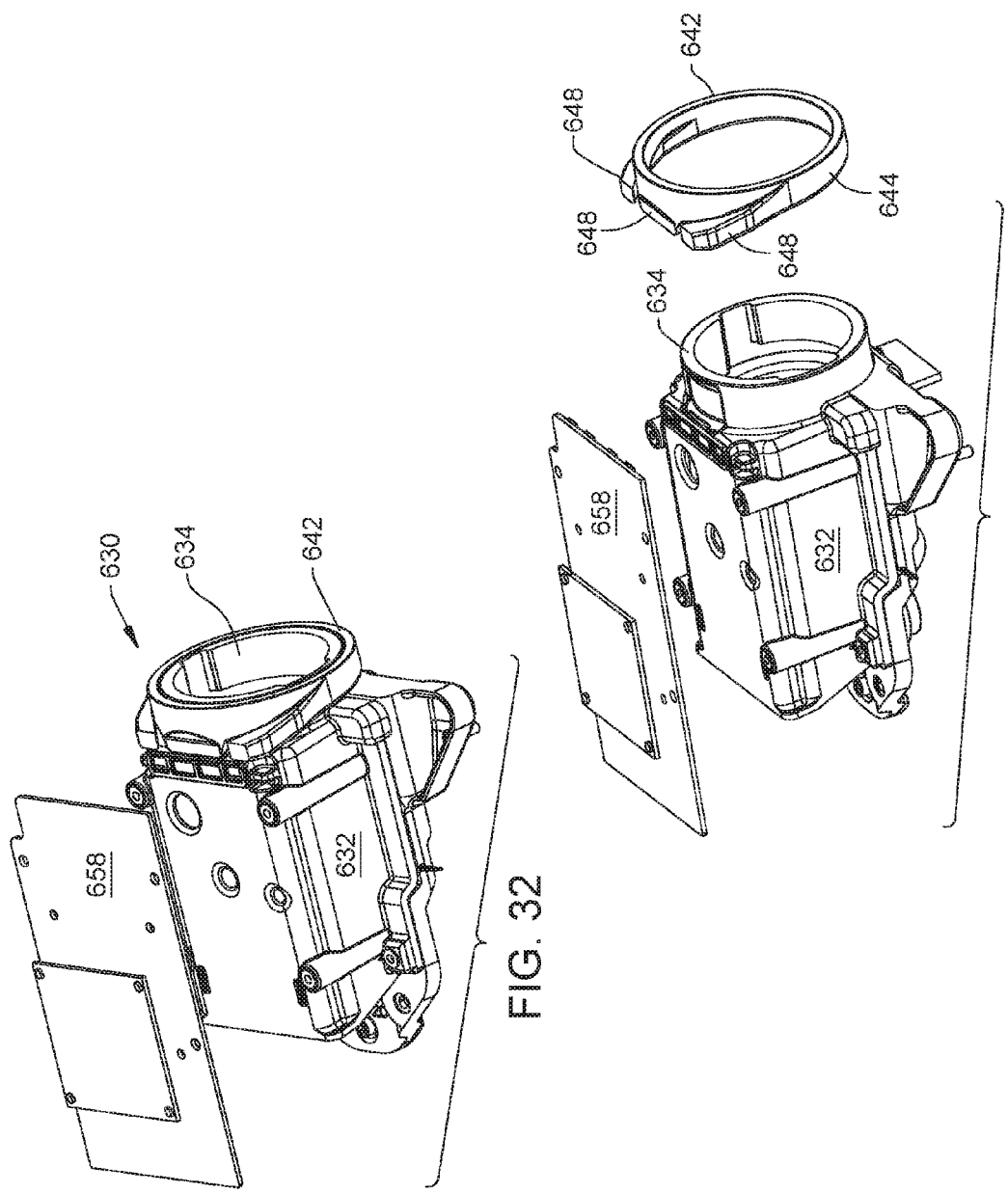

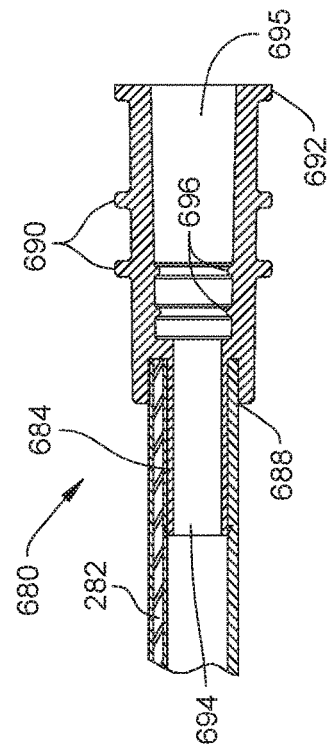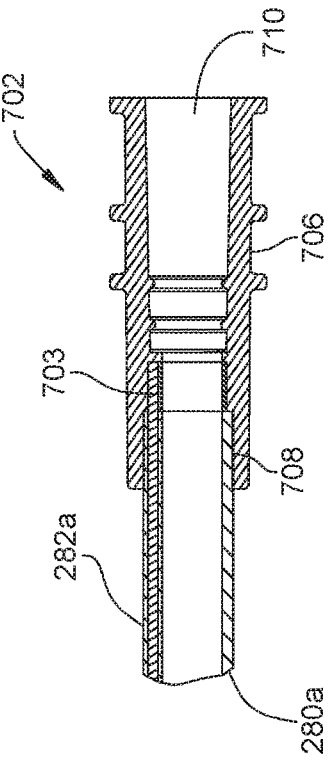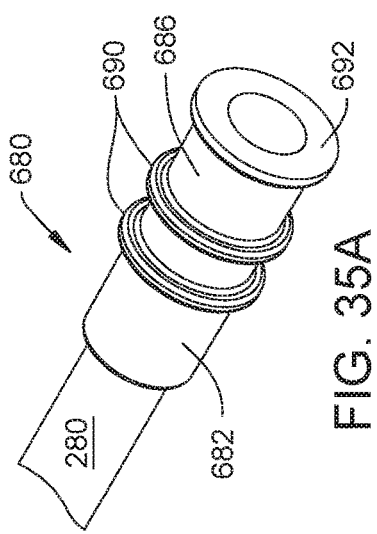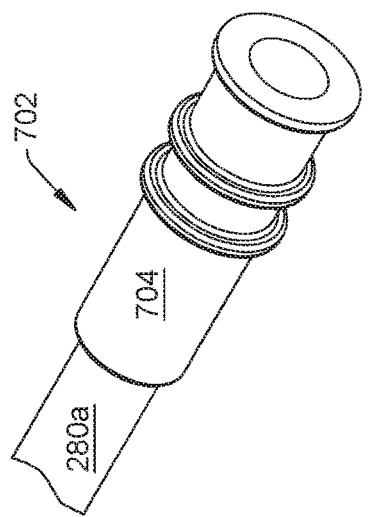

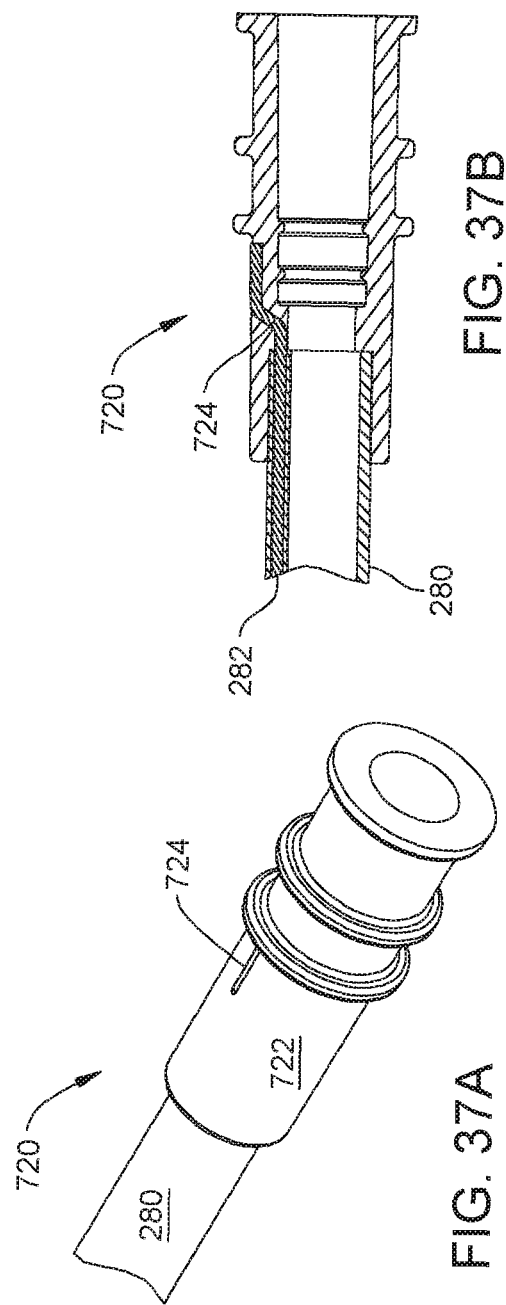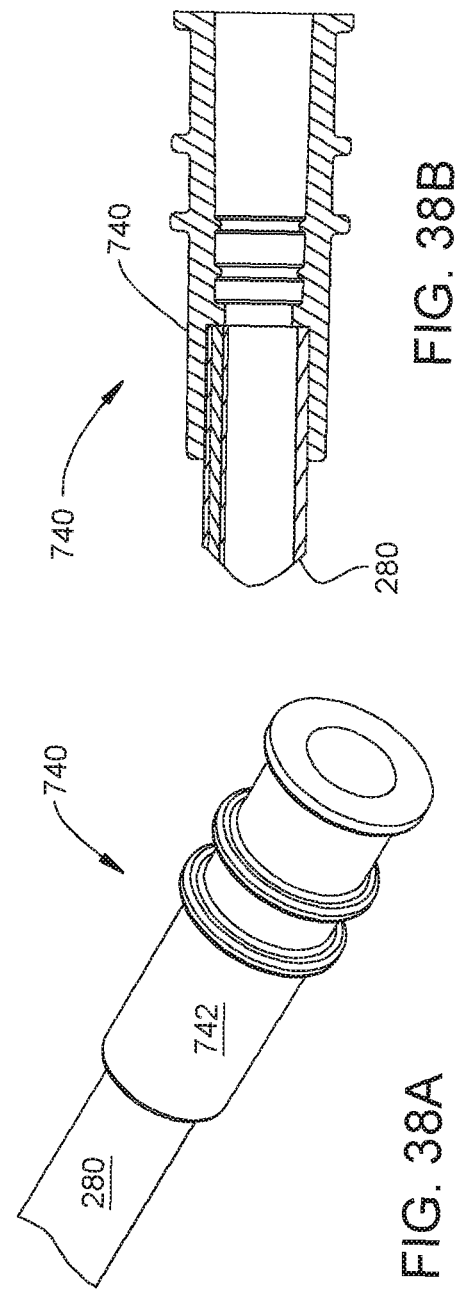

MEDICAL/SURGICAL WASTE COLLECTION UNIT WITH A LIGHT ASSEMBLY SEPARATE FROM THE PRIMARY DISPLAY, THE LIGHT ASSEMBLY PRESENTING INFORMATION ABOUT THE OPERATION OF THE SYSTEM BY SELECTIVELY OUTPUTTING LIGHT

FIELD OF THE INVENTION

This invention is generally related to a system for collecting medical and surgical waste. More particularly, the system of this invention monitors the status of the operation of the waste collection unit and, based on this information, outputs light in different colors and patterns.

BACKGROUND OF THE INVENTION

A byproduct of the performance of some medical and surgical procedures is the generation of liquid and semi-solid waste. This waste includes body fluids, such as blood, and irrigating solution introduced to the body site at which the procedure is performed. This waste also includes bits of tissue and small pieces of the surgical material that may be present at the site. Ideally, the waste is collected upon generation so the waste neither visually obstructs nor fouls the surgical site nor becomes a biohazard in the operating room or other location at which the procedure is being performed.

A number of systems are available for use by surgical personnel for collecting this waste as it is generated. Generally, these units include a suction source, tubing that extends from the suction source and a containment unit between the tubing and the suction source. When the system is actuated, waste is drawn through the distal end of the tubing. The suction draws the waste through the tubing so that it flows into and is stored in the containment unit. One such system is Applicant's NEPTUNE surgical waste collection system. This particular system includes a mobile unit, called a rover, that includes a suction pump and two canisters. Tubing is connected to each canister through a removable manifold. Since the rover is mobile, the rover can be positioned close to the patient on whom the procedure is being performed. This reduces the extent to which the suction tubing, which invariably also functions as operating room clutter, is present around the surgical personnel. Once the procedure is completed, the rover is moved to a static unit called a docker. The docker has couplings that facilitate the essentially automated transfer of the waste collected in the rover to the sewage lines of the facility using the system. This reduces the extent to which operating room personnel are potentially exposed to the materials collected by the system. U.S. Pat. No. 7,621,898, issued 24 Nov. 2009, the contents of which are incorporated herein by reference, describes a number of features of this system.

One of these features is the intake manifold. The manifold is interface between the waste collection unit, the rover, and the sterile suction tubing that extends from the waste collection unit. This manifold includes a filter element that traps solid matter. This is desirable because these solids can potentially clog the downstream components of the system. Moreover, the manifold is formed from material that makes it possible to provide the manifold as a single use item. After use of the system, effort does not have to be spent sterilizing the manifold, with its narrow conduits, or its internal filter. Instead, personnel handling the used manifold only need to contact the outer surface of this component. This process further minimizes the extent to which these individuals potentially are exposed to the waste material. The Applicant's U.S. Pat. No. 7,615,037 issued 10 Nov. 2009, the contents of which are incorporated herein by reference, provided a more detailed description of this type of manifold. Again ideally a new manifold is used with each procedure. Since was not used there is no possibility infectious material from a previous use of manifold can travel down to the suction tube and affect the patient.

The above system is useful for collecting waste collected in a medical/surgical procedure and temporarily storing the waste. The above system also provides a relatively easy means to transport the waste to a transfer station, the docker, for disposal.

The above-described system, like other systems for collecting medical/surgical waste, includes a display panel on which information regarding the operation of the system is presented. This information includes the level of the vacuum draw or the volume of waste that has been collected. For an individual performing a procedure to view this information, the individual must turn his/her away from the patient and towards the display. Having to perform these actions, mentally process the displayed information, and then return his/her head to the patient can interrupt the flow of the procedure.

Also, in some medical and surgical procedures there can be plural lines in the sterile field around the patient through which fluid is drawn into a waste collection unit. One or more of these lines may be lines through which liquid and semi-solid waste is drawn away from the patient. The rover disclosed in the incorporated by reference U.S. Pat. No. 7,621,898, is configured to draw suction through plural suction lines simultaneously such that the suction draw through the individual lines is one of two different suction levels. The rover of U.S. Pat. No. 7,621,898 is also able to do more than draw liquid and semi-solid waste away from the surgical site. This rover has a smoke evacuator. A smoke evacuator, as implied by its name, draws particulate laden air (smoke) away from the surgical site. This smoke is generated in some procedures when electrocautery tools are applied to tissue. The smoke evacuator filters the air to remove the particulates forming the smoke from the air stream prior to discharging the back into the space in which the procedure is being performed. The smoke evacuator reduces the buildup of these particulates as well as the noxious odors generated by the particulates.

An unintended consequence of providing plural tubes to draw away these liquid and gaseous state fluids is that it can be confusing for the personnel performing the procedure to determine which tube is connected to which waste evacuation component. A single tube could be connected to: a component of the system drawing a high vacuum; a component of the system drawing a low suction; or the smoke evacuator. Consequently there may be times during the performance the medical procedure in which the performance of the procedure is slowed so the personnel can verify that the tube being applied to draw away waste generated during the procedure is connected to the sub-assembly of the waste collection system configured to draw away the waste to which the tube is to be applied.

SUMMARY OF THE INVENTION

This invention is directed to a new and useful waste collection system for collecting waste generated during a medical or surgical procedure. The system of this invention presents information about the operating state of the system that is easy to both view and mentally process.

Generally, the system of this invention includes one or more sensors that monitor the state of the operation of the system, sometimes called a waste collection unit. Examples of the monitored states include: the commanded level of the vacuum draw on a particular suction line; the measured level of the vacuum drawn on a particular suction line; the volume of waste in a canister. This information can also include information about the operating state of a smoke evacuator that is part of the waste collection unit. This information includes information regarding: the operating state of the filter integral with the smoke evacuation and information about the operating state of the smoke evacuator. Signals representative of these operating states are applied to a processor.

The waste collection unit of this invention includes a light emitter. This light emitted is separate from and spaced from the display panel through which commands are entered into the waste collection unit. More particularly, the light emitter is in close proximity to the fitting to which the suction line that extend from the waste collection unit is attached. The operation of the light emitter is controlled by the processor. The light display selectively outputs light at different wavelengths (colors). Based on the state information received by the processor the processor causes the light emitter to emit light at different colors or different patterns.

In some versions of the invention, the light output by the light emitter is output to the suction line attached to the waste collection unit. In these versions of the invention, there may be a fiber optic core integral with the suction line. In some versions of the invention, the light is output by the manifold. In some versions of the invention, the light is output to the manifold receiver or other interface between the waste collection unit and the suction line. In some versions of the invention, the light is output to a transparent or translucent structural member that is part of the waste collection unit.

In versions of the invention where the light is sourced to a fiber optic core integral with the suction line, the distal end of the suction tube can be attached to a handpiece with a transparent or translucent component. The light from the fiber optic core is output through the component. This makes the light, and the information represented by the light, visible in the hand of the person holding the handpiece.

The system of this invention provides a means to readily determine information about a state of the system without requiring the individual to look directly at the light emitter. In versions of the invention wherein the light is sourced to a fiber optic core integral with the suction tube, the light is sourced to a location in close in the proximity to the hand of the person performing the procedure. This means that the individual does not have to divert his/her eyes away from the location where the procedure is being performed to perceive the transmitted light. This reduces the extent to which the individual has to break his/her concentration to obtain information about the waste or smoke collection process.

In an alternative version of the invention the light emitter is located in close proximity to the fitting to which the suction line is attached.

A further feature of this invention is that different sub-assemblies of the waste collection unit of this invention will emit light in different colors, in different patterns. When this light is transmitted to a fiber optic core integral with the line connected to the sub-assembly, the light is emitted by the device attached to the distal end of the line. This means that personnel by simply looking at the light emitted by the line or attached device can readily determine the unit sub-assembly to which the line is attached.

BRIEF DESCRIPTION OF THE DRAWINGS

The invention is pointed out with particularity in the claims. The above and further features and advantages of the invention are understood by the following Detailed Description taken in conjunction with the accompanying drawings in which:

FIG. 2 is a perspective view of a suction tube connected to a manifold of this invention and of the manifold seated in the manifold receiver of the waste collection unit;

FIG. 3 is an exploded view of the suction tube, the manifold and the manifold receiver of FIG. 2;

FIG. 8 is an assembly drawing depicted how

FIG. 9 is plan view of the front of a manifold of this invention;

FIG. 10 is a plan view of a side of the manifold;

FIG. 11 is a plan view of the back of the manifold;

FIG. 17 is a perspective view of the back end of the housing of the smoke filter;

FIG. 18 is a perspective view of the inner face of the cover plate of the smoke filter;

FIG. 19 is a view of the front face of the coupler integral with the smoke filter;

FIG. 28 is a perspective view of a manifold seated in an manifold receiver of an alternative version of this invention;

FIG. 29 is a perspective view of the manifold receiver of FIG. 28 with the circuit board mounted to the receiver removed;

FIG. 32 is a partially exploded view of a second alternative manifold receiver of this invention;

FIG. 33 is an exploded view of the manifold receiver of FIG. 32 depicted the top located components of the receiver;

FIGS. 35A and 35B are, respectively perspective and cross sectional view of the distal end of a second alternative suction line of this invention;

FIGS. 36A and 36B are, respectively perspective and cross sectional view of the distal end of a third alternative suction line of this invention;

FIGS. 37A and 37B are, respectively perspective and cross sectional view of the distal end of a fourth alternative suction line of this invention;

FIGS. 38A and 38B are, respectively perspective and cross sectional view of the distal end of a fifth alternative suction line of this invention;

DETAILED DESCRIPTION

I. Waste Collection and Smoke Evacuation Unit

Figure 1:
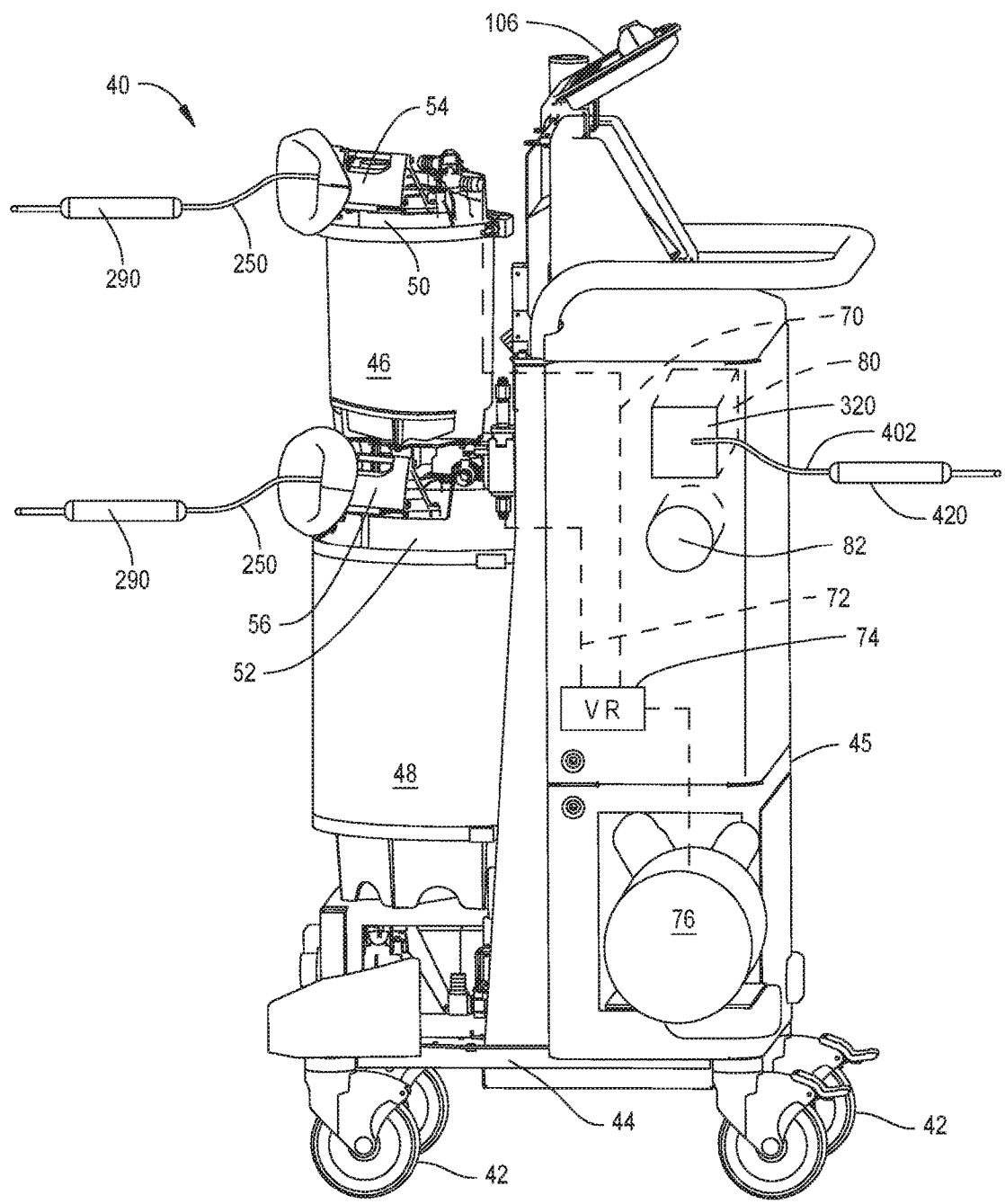
FIG. 1 is side view of a medical/surgical waste collection unit of this invention.

FIG. 1 illustrates a waste collection unit 40 constructed in accordance with this invention. The unit 40, sometimes referred to as a rover, includes a base 44. The cover and doors that normally conceal the components of the unit 40 are not present so that the interior components of the unit can be seen. Wheels 42, attached to the base 44, provide unit 40 with mobility. A chassis 45 extends upwardly from the base 44. The chassis 45 is the structural frame of unit 50 to which other components of the unit are mounted. Two canisters 46 and 48 are mounted to the base 44. Canister 46 is disposed over canister 48. Canister 46 has a relatively small interior volume, between 1 and 10 liters. Canister 48 typically has an interior volume larger than that of canister 46. In some versions of the invention canister 48 has a volume between 10 and 40 liters. Not illustrated and not part of the present invention is a valve located between the canisters 46 and 48. This valve is selectively opened to allow the transfer, the emptying, of the contents of canister 46 into canister 48. A cap, caps 50 and 52, respectively, is disposed over each canister 46 and 48.

Attached to each canister cap 50 and 52 is a manifold receiver 54 and 56, respectively. Manifold receivers 54 and 56 are part of unit 40. Each manifold receiver 54 and 56 releasably holds a manifold 220, seen in FIGS. 2 and 3. The manifold 220 is formed with one or more suction fittings 241. Each suction fitting 241 is dimensioned to receive the proximal end of a suction line 250. ("Proximal" is understood means towards the personnel performing the medical/surgical procedure; away from the surgical site at which the procedure is being performed. "Distal" means away from the personnel performing the procedure; towards the surgical site at which the procedure is being performed.) In FIG. 1 a first suction line 250 is shown extending distally from manifold receiver 54. The distal end of suction line 250 is shown connected to a first suction applicator 290. A second suction line 250 extends distally from manifold receiver 56. The distal end of the second suction line 250 is attached to a second suction applicator 290.

Also part of unit 40 is a vacuum regulator 74 and a suction pump 76. A conduit 70 (shown as a dashed line) extends from canister 46 to the vacuum regulator 74. A conduit 72 (shown as a dashed line) extends from canister 48 to the vacuum regulator 74. In some versions of the invention, the conduit 70 is connected to the canister 46 through cap 50. Conduit 72 is connected to the canister 48 through cap 52. The suction drawn by pump 76 is applied to the vacuum regulator 74. The vacuum regulator 74 controls the vacuum draw through each canister 46 and 48. Vacuum regulator 74 performs this control by selectively applying the suction draw to the canisters and selectively opening the canisters to the ambient environment. By extension, this vacuum control regulates the vacuum draw through the individual suction lines 250. In some versions of the invention, the vacuum regulator 74 sets the vacuum drawn on each canister 46 and 48 independent of the vacuum drawn on the other canister. This means that the vacuum draw, the suction draw, through the suction lines 250 connected to the separate containers can be set to be different from each other.

Not shown and not part of the present invention are the fluid couplings mounted to the unit base 44 below canister 48. The couplings are configured to engage complementary couplings integral with a static unit sometimes referred to as a docker (not illustrated). One of the docker couplings is connected to the sanitary collection piping internal to the facility in which the unit 40 is used. Waste collected in the canisters 46 and 48 is flowed through these couplings out to this piping. A second one of the docker couplings is connected to a water supply line of the facility. Water is supplied from the docker and unit 40 couplings into the canisters 46 and 48 to clean the canisters.

Also part of unit 40 is a smoke evacuator 80. Smoke evacuator 80 includes a smoke filter 320 and a second suction pump, pump 82, both of which are mounted to chassis 45. A smoke line 402 extends from the smoke filter 320. The distal end of smoke line 402 is connected to a handpiece through which smoke is drawn into the smoke evacuator. Owing to the elongated shape of this handpiece and to distinguish this handpiece from other components of this invention, this handpiece is arbitrarily referred to as a smoke pen 420.

Figure 1A:
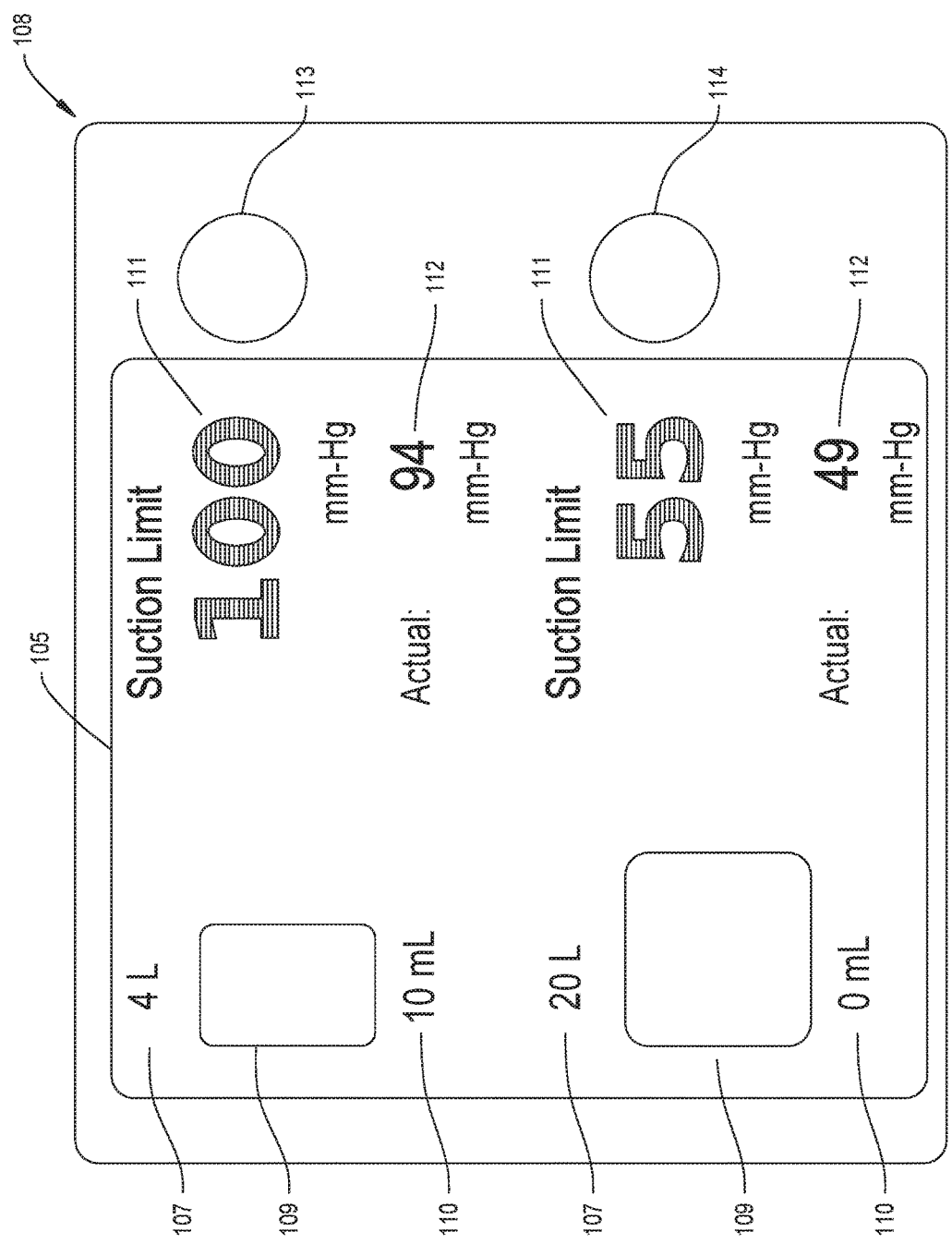
FIG. 1A is a plan view of display panel of the waste collection unit and an image that is presented on the panel.
Figure 5:
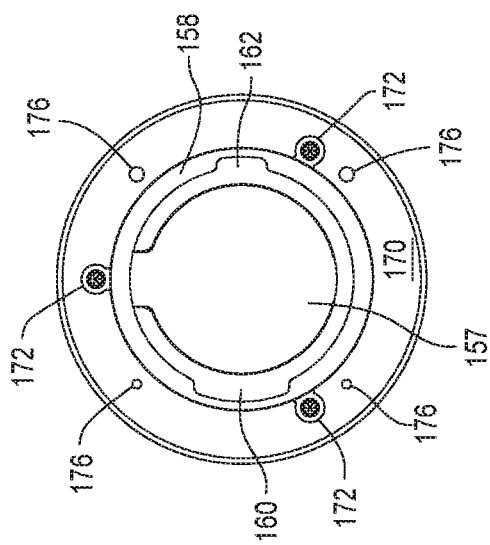
FIG. 5 is a front plan view of the manifold receiver.

A processor 192, (seen in FIG. 8B) controls the operation of unit 40. A display panel 106 is mounted to the base. As seen in FIG. 1A, display panel 106 includes a touch screen 105 through which commands for regulating the operation of unit 40 are entered. The touch screen also functions as a display over which information regarding the operation of the unit is displayed In the depicted version of the invention the images presented on the display include text and representations 107 and 109, respectively of the small and large canisters 46 and 48. There is text 110 associated with each canister 46 and 48 indicating the measured volume of material in the canister. There is text 111 depicting the commanded suction limit for each canister 46 and 48. There is text 112 depicting the measured suction drawn on each canister. The images presented on screen 105 may be in different colors. This is represented in FIG. 1A by the text 111 depicting the commanded suction draws being in a different color than the text 112 representing the measured suction draws.

In the depicted version of the invention, the display panel is shown as also having two rotating knobs 113 and 114. Knob 113 is manually set so to set the maximum setting of the suction draw of canister 46. The text 111 immediately to the left of knob 113 represents the commanded maximum suction draw set by the rotation of the knob 113. Knob 114 is manually set so to set the maximum setting of the suction draw of canister 48. The text 111 immediately to the left of knob 114 represents the commanded maximum suction draw set by the rotation of the knobs 113 and 114.

As seen in FIGS. 2-5, a manifold receiver, arbitrarily, manifold receiver 54, includes a number of static and moving components. One of the static components is a shell 130. Shell 130 is shaped to hold the manifold 220. A second static component is bracket 120. Bracket 120 holds shell 130 to the top of the cap 50 or 52 with which the receiver 54 is associated. Internal to bracket 120 is a bore 128. Bore 128 provides a fluid connection from the proximal end of shell 130 through the cap 50 or 52 into the canister 46 or 48 to which the manifold is mounted. A lock ring 158 is disposed over the distal open end of shell 130. A light ring 170 is disposed over the lock ring.

Manifold receiver shell 130, at least on the outside, is generally cylindrically shaped. Shell 130 is formed to have a center void 132 that extends proximally to distally through the shell. The void 132 is formed by a number of contiguous surfaces internal to the shell that have different radii of curvature (surfaces not identified). Generally it should be appreciated that void 132 is dimensioned to allow the slip fitting of the manifold 220 in shell 130. The depicted receiver shell 130 is shown as having two windows 134. Windows 134 extend through the top of the shell 130 into void 132. Windows 134 are present to facilitate the attachment of the manifold receiver to the associated cap 50 or 52. Windows 134 also provide a space into which the below described door 150 pivots when a manifold 220 is inserted into the receiver 54.

Shell 130 is further formed to have threaded closed end bores 136 (one seen in FIG. 4) that extend distally forward from the proximal end of the shell. Threaded closed end bores 138 (one seen in FIG. 4) extend proximally rearward from the distal end the shell 130.

Bracket 120 is formed from a single piece of plastic that extends from proximally from shell 130. The bracket 122 has a distally directed end face 122 that is disposed against the proximal end of shell 130. Fasteners 123 (one shown) that extend through the bracket 120 into shell bores 136 hold the shell to the bracket. The bracket 120 is formed so that the end face 122 covers the whole of the open proximal end of shell void 132.

The bracket 120 is formed so that a circular boss 124 extends downwardly from the main body of the bracket. Boss 124 is formed to closely fit in a complementary opening formed in the cap 50 or 52 to which the bracket is attached (cap opening not illustrated). An O-ring 126 disposed around the outer surface of the boss 124 provides a seal between the cap 50 or 52 and the boss.

Bracket 120 is formed so that bore 128 is L-shaped. The bore 128 initially extends proximally from an opening in bracket end face 122. This opening in the bracket face it is observed is formed in the face so as to be spaced from longitudinal axis that extends proximal to distally through the shell void 132. This opening is positioned to be spaced away from the center of the bracket end face 122. Bracket 120 is further formed so that bore 128 curves downwardly and extends through boss 124. The proximal end of the bore 128 opens outwardly from the bottom face of boss 124.

The manifold receiver 54 includes a valve plate 142 that is disposed in the proximal end of shell void 132. The valve plate 142 has a circularly shaped body 144. A boss 146 extends forward from the distally directed face of the main body. Boss 146 is formed to have an axially extending through bore 148. The valve plate 142 is formed so that bore 148 has a diameter no greater than the diameter of the opening in the bracket end face 122 from which bore 128 extends.

Valve plate 142 is disposed in the shell void 132 so as to be disposed against the bracket end face 122. The valve plate 142 is able to rotate in the receiver shell 130 between open and closed positions. More particularly, receiver 54 is constructed so that when the valve plate 142 is in the open position, valve plate bore 148 is in registration with the opening into bracket bore 128. When the valve plate 142 is in the closed position, the plate body 144 is disposed over the bracket opening into bore 128.

A door 150 is pivotally mounted to the distal end of receiver shell 132. A spring 152 normally holds the door in the closed position so the door covers the open distal end of shell void 132. Manual force sufficient to insert the manifold 220 into the shell 132 is sufficient to overcome the force the spring 152 imposes on door 150 to hold the door in the closed state. The means by which the door 150 is mounted to the shell 130 and held in the closed position by spring 152 is not part of the present invention.

Lock ring 158 is disposed over the distal front end of the receiver shell 130. The lock ring 158 is generally circularly shaped. The ring is further shaped so as to have a circumferentially extending step 155. Step 155 is the transition surface between the distal portion of the ring, the portion with a small outer diameter and the proximal portion, the portion with a larger diameter (ring portions not identified). The distal portion of the ring has a center opening 157. The ring 158 is further formed to have three equiangularly spaced apart through bores 159, (one seen in FIG. 4). Bores 159 extend proximally from step 155 through the proximal section of the ring 158.

Figure 4:
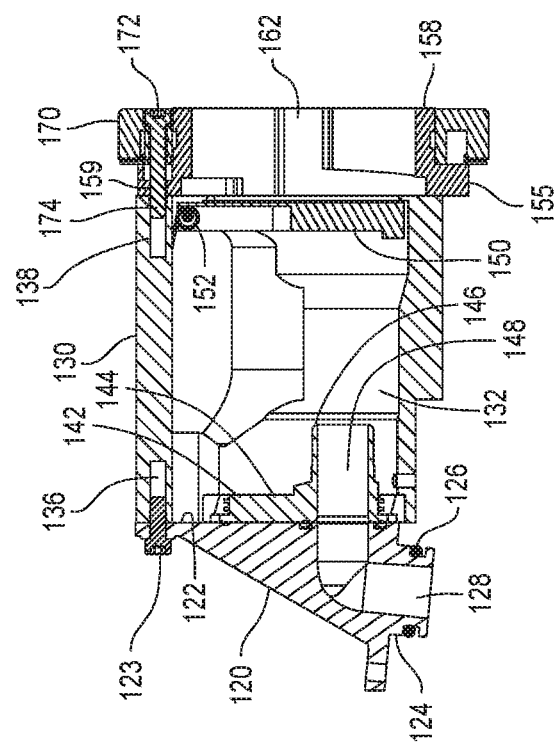
FIG. 4 is a cross sectional view of the manifold receiver taken along line 4-4 of FIG. 2 with the manifold removed.

The lock ring 158 is further formed so that two L-shaped slots 160 and 162 that extend outwardly from the inner surface of the ring that defines the center opening. Each slot 160 has, from the perspective of FIG. 4, a horizontal section and a vertical section. In FIG. 4 only slot 162 is visible. The slot horizontal sections extend from the distal end of the ring to the proximal end. The slot vertical sections are located adjacent the proximal end of the ring 158. The slots 160 and 162 are diametrically opposed to each other relative to the proximal to distal axis through the ring center opening. Slots 160 and 162 are different from each other in that the arc subtended by the horizontal section of slot 160 is greater than arc subtended by slot 162.

The light ring 170 is a ring shaped piece of opaque plastic such as a pigmented polycarbonate plastic. The light ring 170 is dimensioned to seat against lock ring step 155 and around the distal section of the lock ring 158. The light ring 170 is formed to have two sets of bores. There are three bores 172 that are substantially equiangularly spaced apart from each other. Bores 172 each have a counterbore, not identified. The components forming the manifold receiver 54 are formed so that when the receiver is assembled together, the light ring bores 172 are in registration with lock ring bores 159 which are in registration with shell bores 138. Fasteners 174 (one illustrated in FIG. 4) which extend from the light bores 172 through the lock ring bores 159 into the shell bores 138 hold the lock ring and light ring to the shell 130.

Bores 176 are the second set of bores formed in the light ring 170. The light ring 170 is formed to have four equiangularly spaced apart bores 176. Bores 176 extend forward from the proximal end of the light ring. Integral with each bore 176 is a small extension, a light port. The light ports are not identified separately from bores 176. Each light port is smaller in diameter than the associated bore 176 from which the port extends. The light ports extend to the distally directed face of light ring 170. While not shown, the light ports may be covered with, or filled with a piece of optically transparent material such as acrylic. This cover prevents the ingress of water or debris into the light port.

Figure 6:
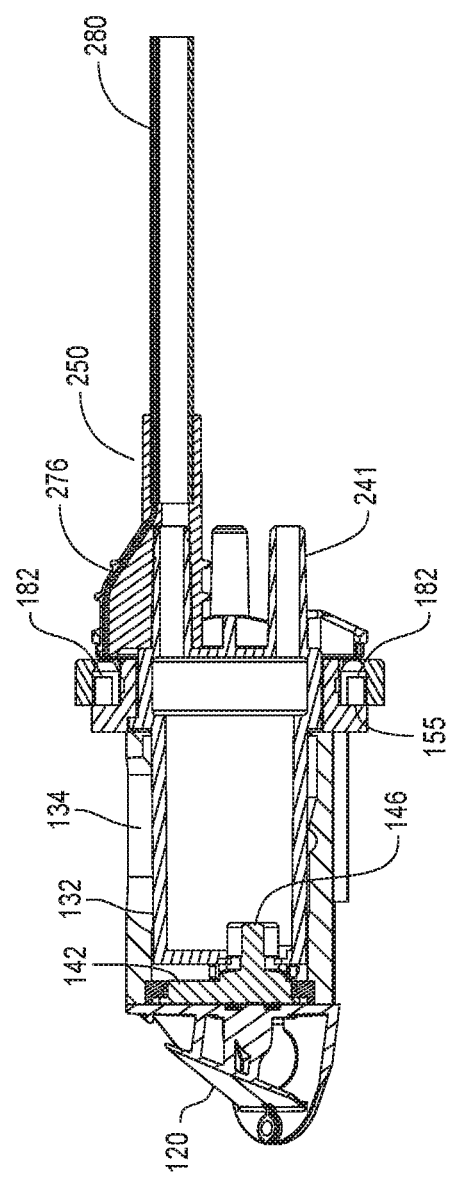
FIG. 6 is a cross sectional view of the manifold receiver with a manifold and suction line attached, taken along line 6-6 of FIG. 2.

An LED 182 capable of emitting light at different wavelengths, different colors, is seated in each bore 176. (Two LEDs 182 seen in FIG. 6.) LEDs capable of functioning as the LED 182 are found in the Xlamp (R) LED Family available from Cree, Inc. of Durham. N.C. These LEDs are capable of emitting visible light of the following colors: red; green or blue. These lights are capable of simultaneously emitting each of these so as to emit light that is blend of two or three of these colors.

Figure 7:
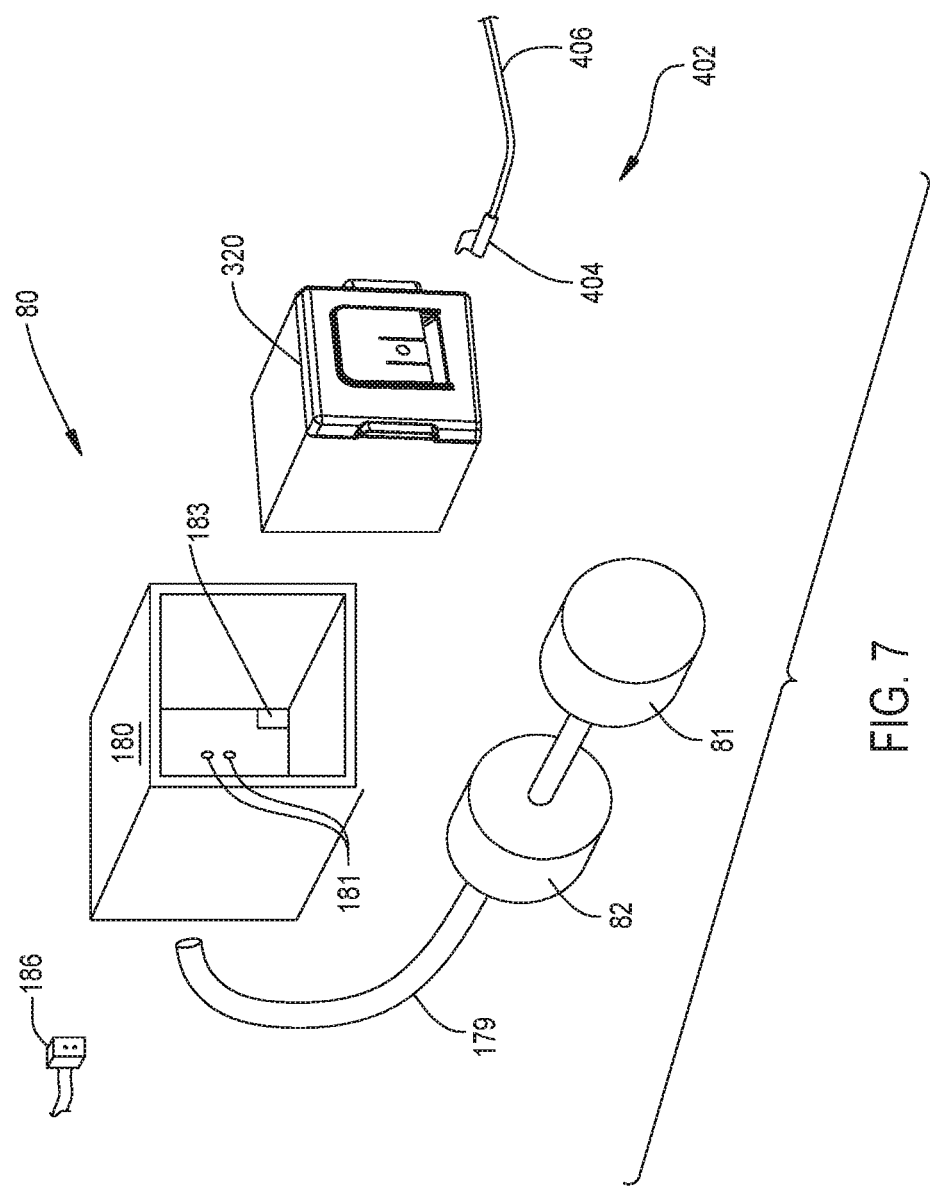
FIG. 7 is an exploded view of the components forming the smoke evacuator of this invention.

As seen in FIG. 7, the unit smoke evacuator 80 includes a generally rectangularly shaped filter receptacle 180. The filter receptacle 180 is mounted to the chassis 45 by a means not shown. While not identified it is understood that the filter receptacle 180 is shaped to have an open end and an opposed closed end. Filter receptacle 180 is shaped to receive the smoke filter 320. Two openings 181 are shown in the closed end of receptacle 180. A vacuum hose 179 extends from openings 181 to the suction pump 82. The number of openings 181 is not part of the present invention. Filter receptacle 180 is also shown to have a rectangular opening 183. Opening 183 is located in one corner of the end plate of the receptacle 180.

Suction pump 82 is also mounted to the chassis 45 by a means not shown. The suction pump 81 is driven by a motor 81 also mounted to the chassis by a means not illustrated and not part of the present invention. Motor 81 is a variable speed motor. By extension this means that by varying the speed of motor 81 it is possible to vary the level of the vacuum drawn through the smoke pen 420 and smoke line 402.

A socket 186 is mounted in the filter receptacle opening 183. Socket 186 has contacts (not illustrated). When the smoke filter 320 is seated in the receptacle 180, contacts integral with the plug 388 that is part of the filter 320 engage the complementary contacts integral socket 186.

Figure 8A:
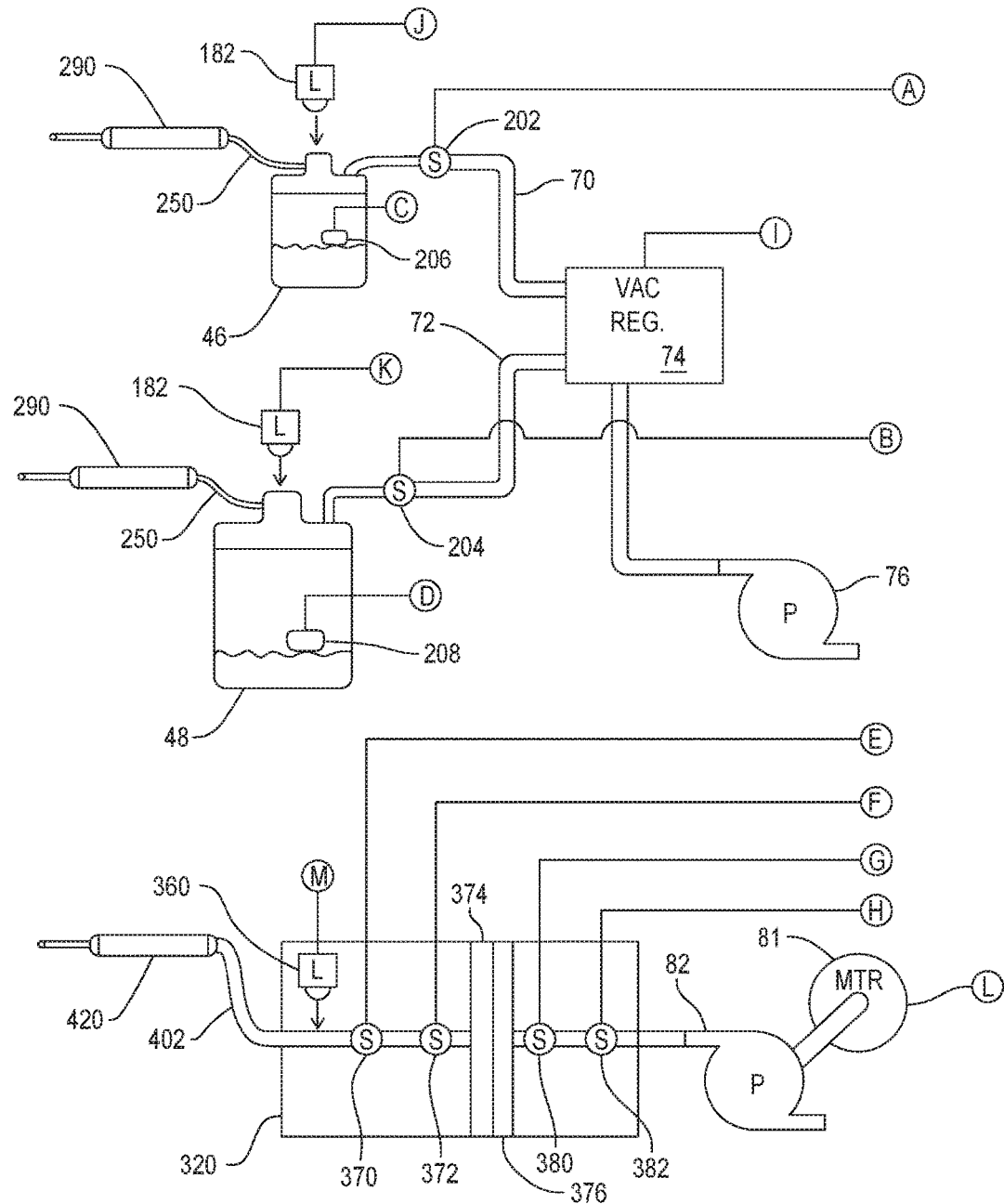
FIGS. 8A and 8B are placed together to form a block diagram of the electrically active components of the waste collection unit of this invention.
Figure 8B:
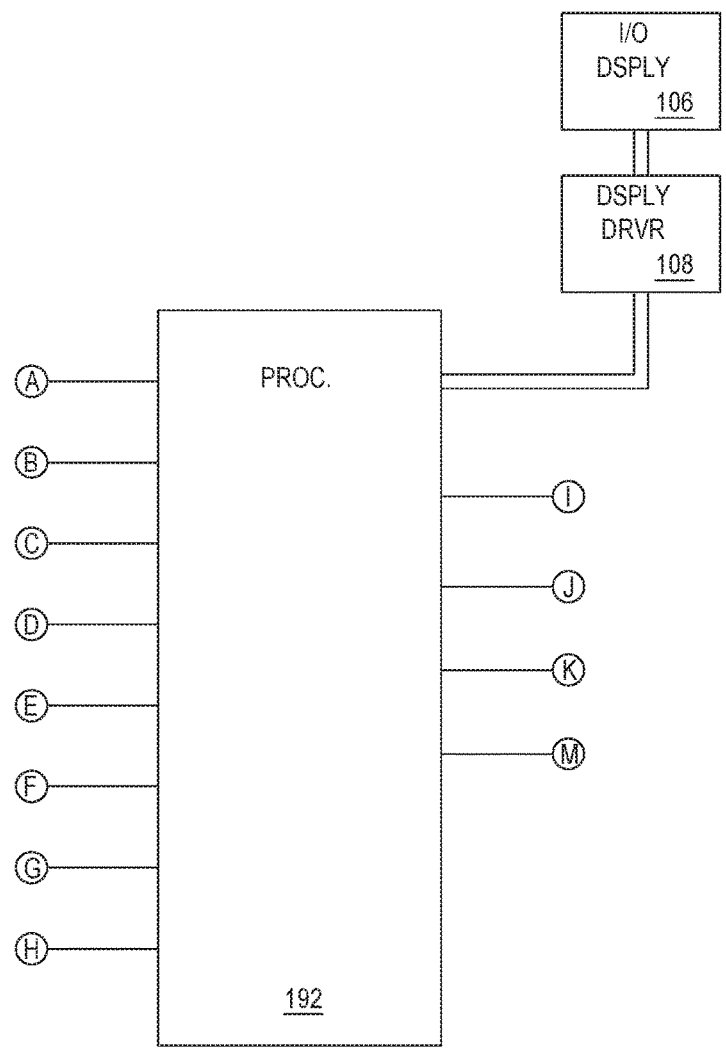

FIGS. 8A and 8B, when assembled together, form a block diagram of the basic electrically active and electric controlled components of unit 40 of this invention. These components include display panel 106, I/O DISPLY in FIG. 8B. The images presented on the display panel 106 are generated by a display driver 108. The display driver 108 also generates output signals representative of the commands entered through the display 106 by the depressing of control buttons presented on the display and the setting of knobs 116. The display driver 108 is connected to the processor 192. Processor 192 receives from the driver 108 the signals representative of the commands entered through display panel 106. The processor 192 generates the instructions to the display driver 108 that direct the driver to cause specific images to be presented on the display 106.

Unit 40 also includes two vacuum sensors, sensors 202 and 204. Sensor 202 monitors the vacuum drawn on canister 46. By extension, this is the vacuum drawn on the suction line 250 connected to the canister 46. Sensor 204 monitors the vacuum drawn on canister 48. By extension, this is the suction drawn on suction line 250 connected to canister 48. In FIG. 8A, the sensors 202 and 204 are shown connected to the conduits 70 and 72, of the associated canisters 46 and 48, respectively. This is for purposes of illustration only. In practice the sensors 202 and 204 may be attached to any location in the fluid path associated with the canister 46 and 48 at which it is possible to obtain a measure of the suction draw. Alternative locations include the top of caps 50 and 52 or any other point along the suction path. The output signals representative of the measured suction draws are output by sensors 202 and 204 to the processor 192.

Shown symbolically on the surface of waste collected in canister 46 is a float 206. Shown symbolically on the surface of waste collected in canister 48 is a float 208. Floats 206 and 208 represent that the waste collection unit also includes assemblies for measuring the volumes of waste stored in the canisters 46 and 48. The volume measuring assemblies generate signals representative of the sensed volume that are also output to processor 192.

As discussed in more detail below, internal to the smoke filter 320 are four sensors. Two sensors, sensors 370 and 372, are upstream of the filter elements 374 and 376. The remaining two sensors, sensors 380 and 382, are located downstream of the filter element 374 and 376. Sensors 370 and 380 monitor the amount of smoke present in the air stream that is, respectively, upstream and downstream, of the filter elements 374 and 376. Sensors 372 and 382 monitor the pressure of the air stream upstream and downstream of filter elements 374 and 376. The output signals produced by sensors 370, 372, 380 and 382 are output through plug 388 and socket 182 to the processor 192.

Processor 192 asserts output signals that control a number of the components waste collect unit 40. One of these components controlled by the processor 192 is the vacuum regulator 74. The inputs variables upon which control of the vacuum regulator 74 is based are the suction level commands entered through the display 106 and measured suction draw levels. Based on these inputs, processor 192 causes the vacuum regulator 74 to establish the levels of vacuum drawn on suction lines 250. The means by which these vacuums are drawn is not part of the present invention. However, for background purposes it should be understood that in one version of the invention, the vacuum regulator operates by selectively: connecting the canister 46 or 48 being regulated to: the vacuum pump 76; the ambient environment; or neither the pump nor the ambient environment. Vacuum regulator 74 is able to set the vacuum draw level of each canister 46 and 48 independently of the suction draw of the other canister 48 and 46.

Processor 192 may control the on/off state of suction pump 76. This connection is not shown in the drawings. This is because above, in the described version of the invention the level of vacuum draw through the suction applicators 290 is not regulated by regulating the vacuum draw of pump 76.

Accordingly, to simplify the description of the invention, it is assumed that when unit 40 is actuated, pump 76 is automatically turned on and draws a vacuum at a generally constant level.

Processor 192 is further able to regulate the level of the vacuum drawn by smoke evacuator 80. In the described version of unit 40, the processor 192 performs this regulation by regulating the speed of motor 81. The circuit by which processor 192 regulates motor speed is not part of the present invention.

The processor 192 also regulates the emission of light from the LEDs 182 and 360. To simplify FIG. 8A, only a single LED 182 is shown associated with each canister 46 and 48. It is understood that unit 40 is configured so that all the LEDs 182 associated with each canister 46 and 48 emit the same color of light simultaneously.

II. Waste Collection Manifold

The manifold, now described by reference to FIGS. 3, 9, 10 and 11, includes an open ended shell 222. A cap 230 covers the open distal end of the shell 158. Collectively, shell 222 and cap 230 form the body of the manifold 220. (In FIG. 6, for ease of illustration, shell 222 and cap 230 are shown as a single piece unit.) Internal to this body is a void space (not identified). Shell 222 has a disc shaped base 223. A tubular shaped side wall 226 extends distally forward from the base. The shell 222 is further formed so as to have an opening 224 in the base 223. Manifold 220 is constructed so that valve plate boss 146 can seat in the opening 224. For reasons not relevant to this invention, a lip 225 extends around opening 224. The shell side wall 226 is dimensioned to allow the manifold 220 to seat in the void 132 internal to receiver shell 130.

The manifold cap 230 has a tube shaped skirt 232. The cap skirt is dimensioned to seat over the open distal end shell wall 226. Not illustrated and not part of the invention are the features integral with the shell 222 and cap 230 that hold these components together. Two diametrically opposed tabs 234 and 235 extend radially outwardly from the proximal end base of the skirt. Tab 234 subtends a relatively large arc and is dimensioned to seat in slot 160. Tab 234 is not able to seat in slot 162. Tab 235 subtends a smaller arc and is able to seat in slot 162.

A head 236 formed integrally with the skirt 232 extends over the distal end of the skirt. Head 236 is generally circular in shape and extends radially outwardly from the perimeter of the skirt. While the head 236 is generally circular, the head is not completely circular. The head 236 is formed with four equiangularly spaced apart indentations 238 (two identified). Indentations 238 facilitate the griping and rotating of the manifold by the thumb and fingers. A rim 240 projects outwardly from the perimeter of the head circumferentially around the head. The rim 240, like the indentations 238, facilitates the gripping and rotating of the manifold. The disclosed manifold is shown as having four fittings 241. Each fitting 241 opens into the void space internal to the manifold 220. While not apparent from the drawings, the manifold 220 may be formed so that the outer diameter of each fitting 241 tapers outwardly relative to the diameter of the fitting at the distal end of the fitting. Four webs 239, (two webs 239 identified,) also extend outwardly from head 236. Webs 239 radiate outwardly from the center of head and are equiangularly spaced apart from each other. Each web 239 extends between two fittings. The outer end of each web 239 abuts a portion of rib adjacent one of the indentations 238.

A pair or webs 244 extend outwardly from each fitting 241, one pair of webs identified in FIG. 9. Webs 244 come together at the inner surface of the section of rim 240. Each pair of opposed webs defines a hollow 242 above the top surface of cap head 236. The cap 230 is further formed so that rim 240 and webs 242 extend outwardly beyond the cap head 236. Thus where the radial outermost portions of each pair of webs defines an opening 243. Two openings 243 identified in each of FIGS. 9 and 11.

The manifold 220 typically has other features that are not part of this invention. To avoid confusion these features are not illustrated. These features include one-way valves that allow flow through each fitting 241 into the manifold and that block the reverse flow. A filter is often disposed in the manifold. The filter blocks the flow of solid waste into the canister 46 or 48 with which the manifold is disposed. A drip stop is typically mounted to opening 224. The drip stop prevents flow out of the opening 224 unless the valve plate boss 146 is seated in the opening.

III. Suction Line

Figure 12:
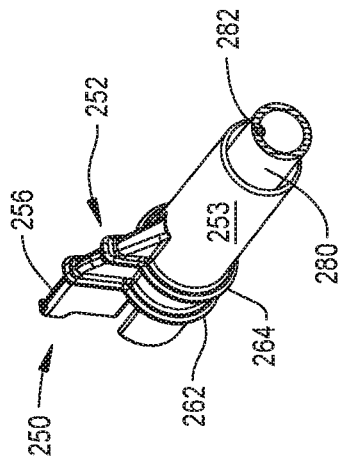
FIG. 12 is a perspective view of suction line of this invention wherein the line is viewed from the proximal end of the proximal fitting.
Figure 13:
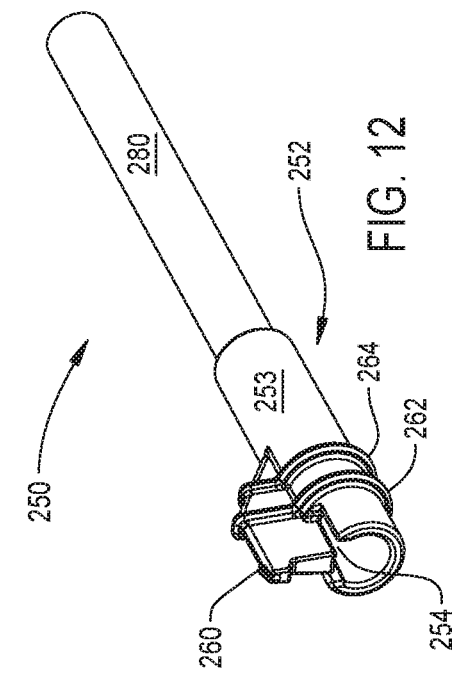
FIG. 13 is a perspective view of the suction line wherein the distally directed face of the proximal fitting is viewed.
Figure 14:
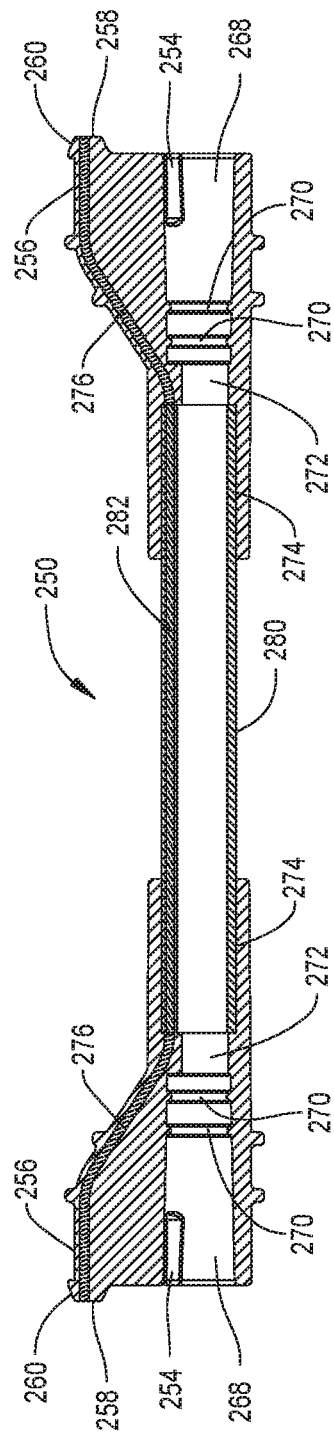
FIG. 14 is a cross sectional view of the suction line.

From FIGS. 12-14 it can be seen that suction line 250 includes a fitting 252 from which a tube body 280 extends. The fitting 252 is formed from an elastomeric material, such as silicone rubber. Fitting 252 is shaped to form a tube shaped sleeve 253. The fitting 252 is dimensioned so that the lumen that extends axially through the sleeve 253 can receive a manifold fitting 241. The proximal end of sleeve 253 is shaped to have a notch 254. A fin 256 extends radially outwardly from sleeve 253. Fin 256 emerges outwardly from a portion of the sleeve 253 adjacent the minor axis, the lateral axis, through the sleeve. Extending proximally from this location, the height of the fin 256 relative to the surface of the sleeve 253 increases so as to provide the fin a taper. From a location approximately half way along the sleeve to the proximal end of the sleeve, fin 256 is generally a constant height. The fin 256 projects into the space above notch 254. The sides of the fin 256 are spaced inwardly from the opposed surfaces of sleeve 253 that define notch 254. Thus, there is a gap between each side of the fin 256 and the adjacent notch-defining surface of the sleeve 253. The width of the fin 256 is such that the fin can seat in one of the hollow 242 located above manifold head 236. Fitting 252 is further formed so that a foot 258 projects proximally rearwardly from the outer end of the proximally directed face of the fin 256.

Fitting 252 is further formed to have tab 260 that projects outwardly from the surface of the fin 256 that is part of foot 258. The tab 260 is tapered such that the distance of the tab from the center of sleeve 253 increases moving distally forward along fin 256. The components of this invention are further constructed so that when the tube fitting sleeve 253 is initial seated over the manifold fitting 241, the fin 256 seats in the hollow 242 above the manifold head 236. A further feature of fitting 252 is that the portion of the fin 256 that extends into notch 254 is able to flex relative to sleeve 253.

The fitting 252 is further formed to have two outwardly projecting ribs 262 and 264. The proximalmost rib, rib 262, extends outwardly from sleeve 253 and fin 256 at a location slightly forward of the distal end of notch 256. The distal rib, rib 264, is located approximately midway between the location from which the fin 256 emerges from the sleeve and rib 262. Ribs 262 and 264 facilitate the gripping of the fitting 252 to facilitate the attachment to and disconnection of the suction line 250 to the waste collection unit 30.

The lumen through fitting sleeve 253 consists of three contiguous bores. A proximal bore, bore 268 extends forward from the proximal end of sleeve 253. Fitting 252 is shaped so that the diameter of bore 268 is approximately 0.25 mm greater than the outer diameter of the manifold fittings 241. While not apparent from the drawings, the fitting sleeve 253 may be formed so that bore 268 has a slight inward taper relative to the proximal end opening into the bore. The fitting 252 is further shaped so that internal to sleeve 253 two ribs 270 extend circumferentially inwardly from the inner wall of the sleeve that defines bore 268. The inner diameters of ribs 270 are approximately 1 mm less than the outer diameter of a manifold fitting 241. When a suction line 250 is mated to a fitting 241, ribs 270 form a seal that prevents the suction loss between these components. Bore 268 opens into a bore 272. Bore 272 has a diameter less than the diameter of bore 268. The longitudinal axis of bore 272 is laterally offset from the longitudinal axis of bore 268. More particularly the longitudinal axis of bore 272 is located further from fin 256 than the longitudinal axis of bore 268. The distal end of bore 272 opens into a bore 274. Bore 274 is coaxial with bore 268. Bore 274 has a diameter approximately 3 mm greater than the diameter of bore 268. Thus, while not identified, there is a step internal to sleeve 253 between bore 272 and bore 274. Bore 274 forms the distal end opening into sleeve 253.

Fitting 252 includes a fiber optical core 276. Core 276 extends forward from the proximally directed face of foot 258. Foot 258 it is observed projects outwardly beyond the fitting sleeve 253. Thus it is understood that the proximally directed exposed end of core 276 is located proximal to the proximal end of the fitting sleeve 253. The core 276 extends through the fin 256 into a portion of sleeve 253 forward of the fin. The core 276 terminates in the step internal to the sleeve 253 between bores 272 and 274. Not identified is the channel internal to the sleeve 253, fin 256 and foot 258 through which the fiber optic core 276 extends.

Tube body 280, as implied by its name, is tubular in structure. The tube body 280 is formed from transparent flexible plastic such as a polyvinyl chloride plastic. Internal to the tube body is a fiber optic core 282. Fiber optic core 282 may be formed from flexible transparent material such as an acrylic. The proximal end section of tube body 280 is seated in fitting bore 274. More particularly the proximal end face of the tube body 280 is disposed against the step internal to the fitting sleeve 253 between bores 272 and 274. The tube body is positioned in the bore so that fiber optic core 282 integral with the tube body 280 abuts fiber optic core 276 internal to fitting 252.

As seen from FIG. 14, a second fitting 252 may extend forward from the distal end of tube body 280. This second fitting is connected to the suction applicator 290 to which the line 250 is connected.

IV. Suction Applicator

Figure 15:
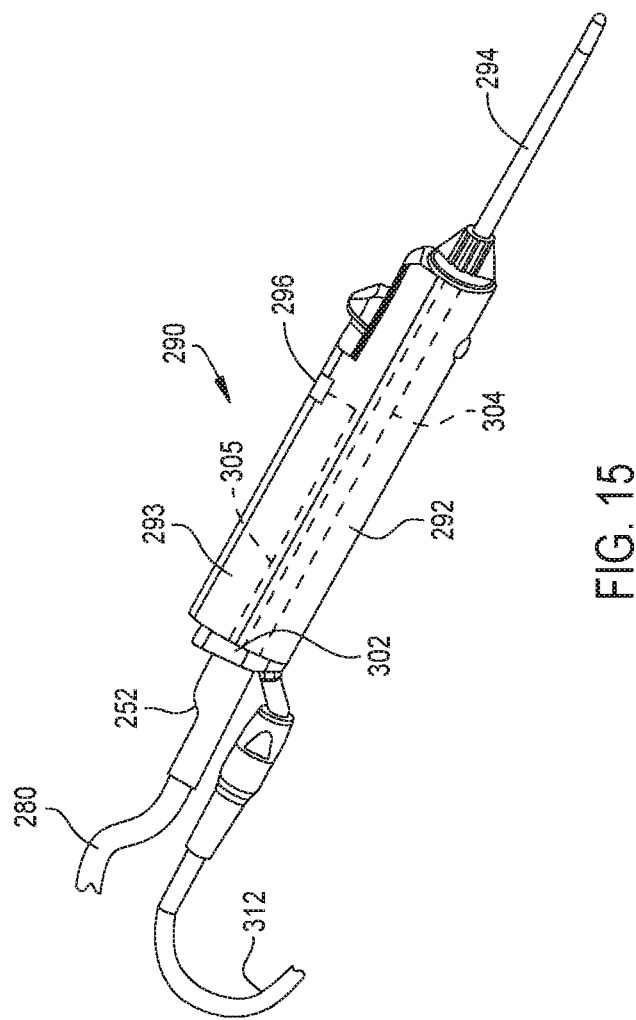
FIG. 15 is a perspective view of one suction applicator of this invention.

FIG. 15 illustrates one type of suction applicator 290 that may be part of the system of this invention. The particular suction applicator 290 is a powered surgical tool. The tool includes a handpiece 292 shaped to be held in the hand. Handpiece 292 includes a housing 293 that forms the body of the handpiece. A cutting accessory 294 extends forward from handpiece housing 293. Possible cutting accessories are shavers, burs and drill bits.

A motor (not illustrated) is disposed in the handpiece housing 293. The motor drives the cutting accessory 294. Handpiece 292 also has a block 296 formed from translucent material. Block 296 is seated in a notch formed in the housing 293 (notch not identified). In the illustrated version of the invention, the handpiece 292 is constructed so that block 296 is located closer to the cutting accessory 294 than the proximal end of the housing 293.

A suction coupling 302, seen as a block in FIG. 15, is affixed to the proximal end of housing 293. Coupling 302 is shaped to receive the fitting 252 that forms the distal end of the suction line 250. Internal to the handpiece 292 is a suction lumen 304 (shown as a pair of dashed lines). The suction lumen 304 extends from the outlet port integral with coupling 302 distally through the handpiece 292. Suction lumen 304 opens into a complementary suction lumen in the cutting accessory 294 (accessory suction lumen not shown).

A fiber optic core 305 (shown as a dashed line) is also disposed in the handpiece housing 293. Fiber optic core 305 extends from the portion of the coupling against which the fitting foot abuts into the housing 293. The fiber optic core 305 terminates at block 296.

Both suction line 250, and a cable 312 are shown connected to the proximal end of the handpiece. Cable 312 is connected to a console (not illustrated and not part of the invention). The console sources the power signals that are applied to the handpiece motor over the cable 312.

V. Smoke Filter

Figure 16:
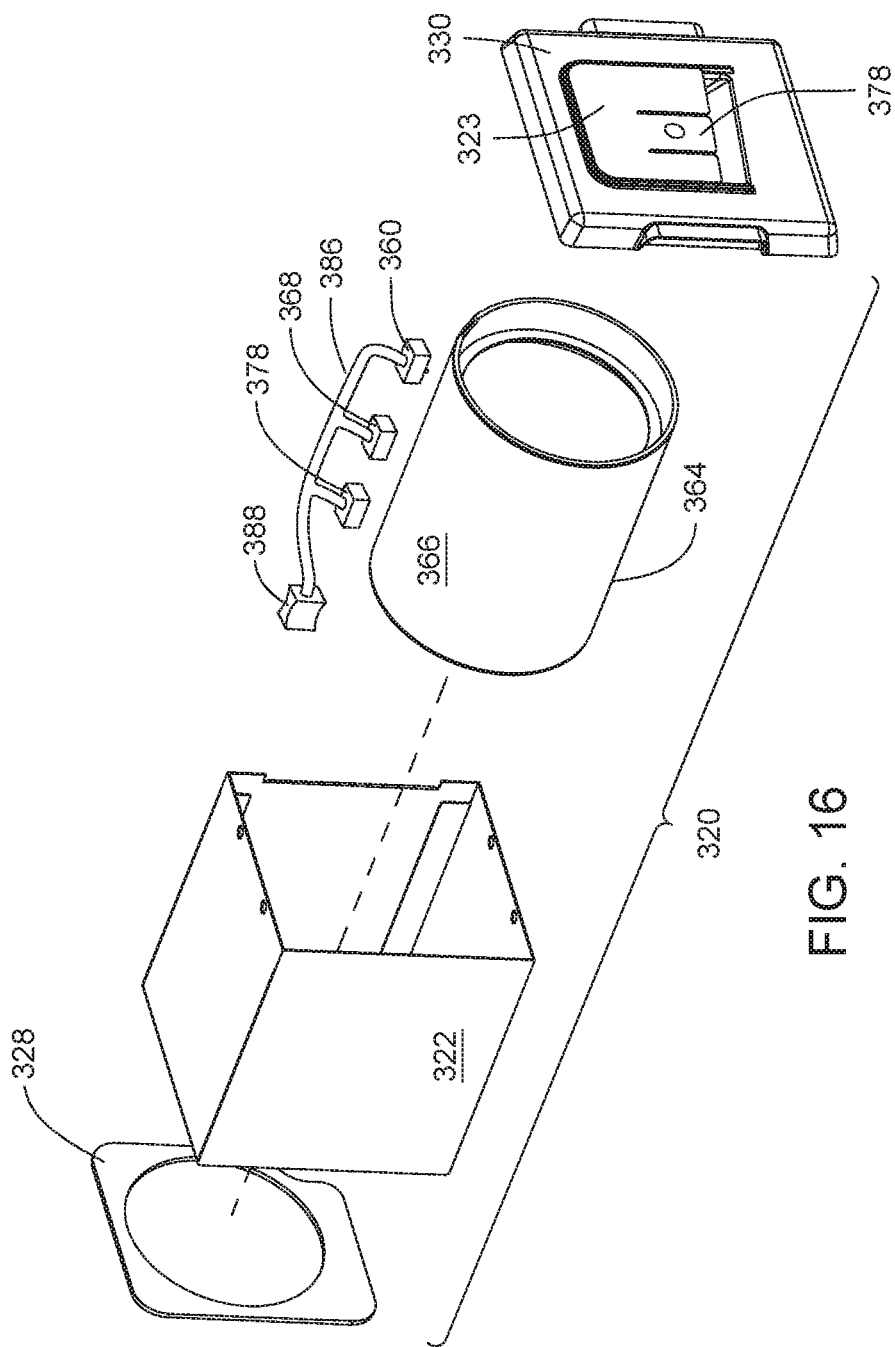
FIG. 16 is an exploded view of some of the components of smoke filter of this invention.
Figure 20:
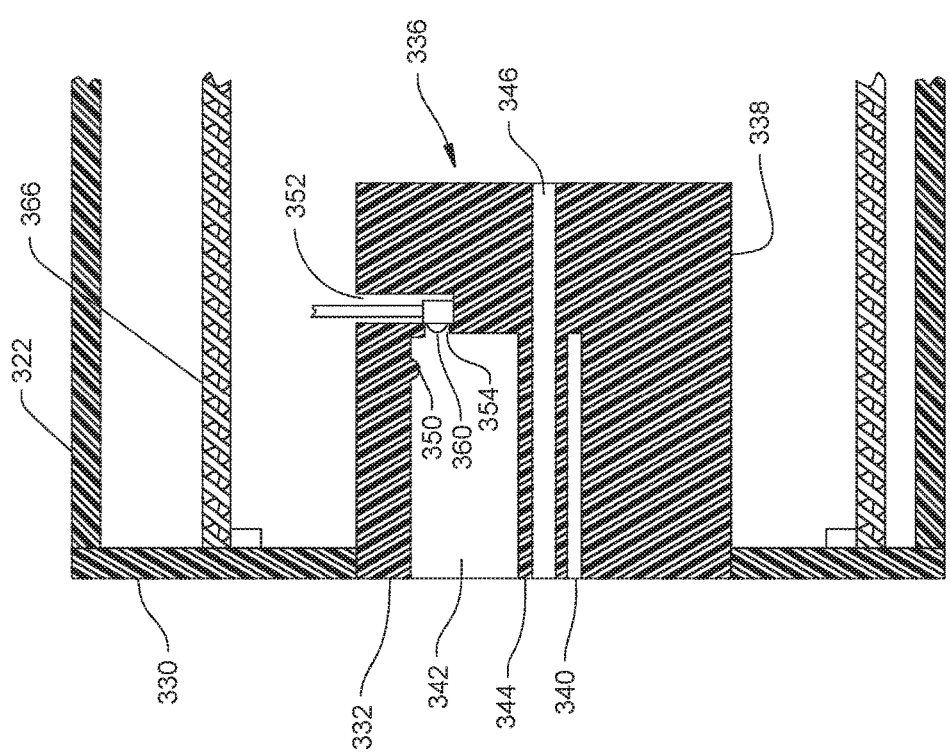
FIG. 20 is a cross sectional view of the front end of the smoke filter.

A smoke filter 320 of this invention is now described by initial reference to FIGS. 16-18. The filter 320 includes a filter housing 322 that is generally rectangularly shaped. More particularly, filter housing 322 is dimensioned to fit in receptacle 180 integral with the smoke evacuator 80. The distal end of the housing is open. Integral with the proximal end of the housing is an end plate 324. The end plate 324 is formed to define a circular opening 326. Opening 326 occupies most of the surface of the area subtended by the perimeter of the end plate 324. Adjacent one corner of the end plate 324 there is a small rectangular opening, opening 327. A compressible seal 328 is disposed around the outer, proximal facing surface of the end plate 324. Seal 328 prevents suction loss between smoke filter 320 and the adjacent wall of the receptacle 180 against which the filter is disposed. A face plate 330 is disposed over the distal open end of the housing 322. A filter assembly 364 and a wire harness 386 are disposed inside the filter housing 322.

The face plate 330, now described in more detail with reference to FIGS. 16, 18 and 19, is shaped to fit over the open end of filter housing 320. Generally the face plate 330 has opposed exposed, distal facing and concealed, proximal facing, surfaces. Not described are the features of the face plate that facilitate the attachment of the plate to the filter housing 320 and/or that facilitate the instillation and removal of the smoke filter to and from receptacle 180. The face plate 330 is further formed to have an opening 332.

A cover panel 323 is disposed over the distal facing exposed surface of the face plate 330. Cover panel 323 is in part cosmetic and may contain instructions for operating the unit. The cover panel 323 includes a planner flapper tab 325 that is able to flex relative to the rest of the panel. Flapper tab 325 normally covers the bore in the below described coupler 336 in which the smoke line proximal fitting 404 is inserted.

Figure 22:
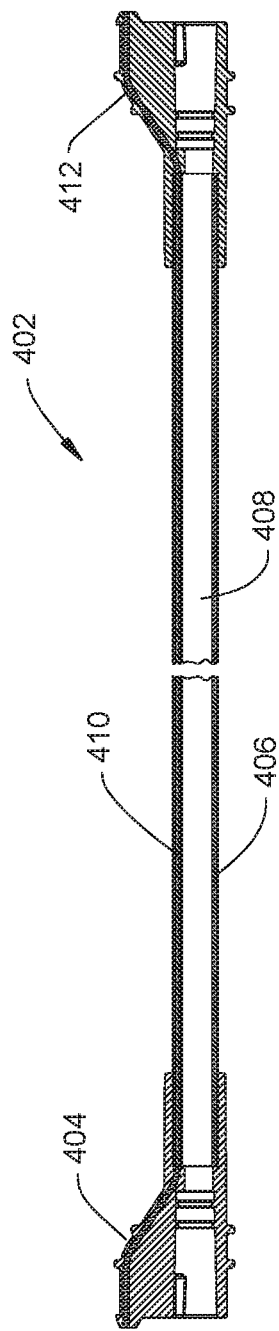
FIG. 22 is a cross sectional view of a smoke tube of this invention.

A coupler 336 is fitted in the face plate opening 332 so as to project inwardly from the concealed surface of the plate 330. Coupler 336 is the component of smoke filter 320 to which smoke line 402 is connected. The coupler 336 has a body 338 that is generally in the form of a cylinder. The body 338 is formed to have a closed end bore that extends inwardly from the outer face of the bore. The bore has a lower section, bore section 340. Bore section 340 is generally circular in shape when viewed from the front of the body. The bore section 340 is shaped to receive the cylindrical portion of smoke evacuation line proximal fitting 404 (FIG. 22). An elongated slot section 342 extends upwardly from section 340. Slot section 342 is shaped to receive the fin of proximal fitting 404. The coupler body 338 is further formed so that that a tube like fitting 344 projects forward from the wall of internal bore section 340 that defines the base of the bore. Fitting 344 extends into bore section 340. The fitting is dimensioned to seat in the lumen at the proximal end of the smoke evacuation tube fitting. Fitting 344 has an axially shaped lumen 346. An extension of the lumen 346 extends proximally out through the back face of coupler body 338.

The coupler body 338 is further formed to have a small tab, tab 350. The tab 350 projects into the section of slot 342 that is spaced from bore 340. Coupler body 338 is formed with an additional closed end bore, bore 352. Bore 352 extends downwardly from the top of the coupler body 338. The bore 352 terminates at a location immediately rearward of the end of slot section 342 that is spaced from bore section 340. The coupler body 338 has an opening 354 that extends through the portion of the body that separates slot 342 from bore 352. Collectively, the components of this invention are shaped so that when proximal fitting 404 is seated in the coupler body, body tab 350 is located forward of the tab integral with the fitting fin so as to hold the smoke line 402 to the smoke filter 320. The exposed end of the fiber optic core internal to the fitting fin is in registration with opening 354 internal to the coupler body 338.

An LED 360 capable of emitting light at different wavelengths, of different colors, is disposed in coupler body bore 354. The LED 360 is positioned so the light emitted by the LED is emitted through coupler body opening 354.

Figure 21:
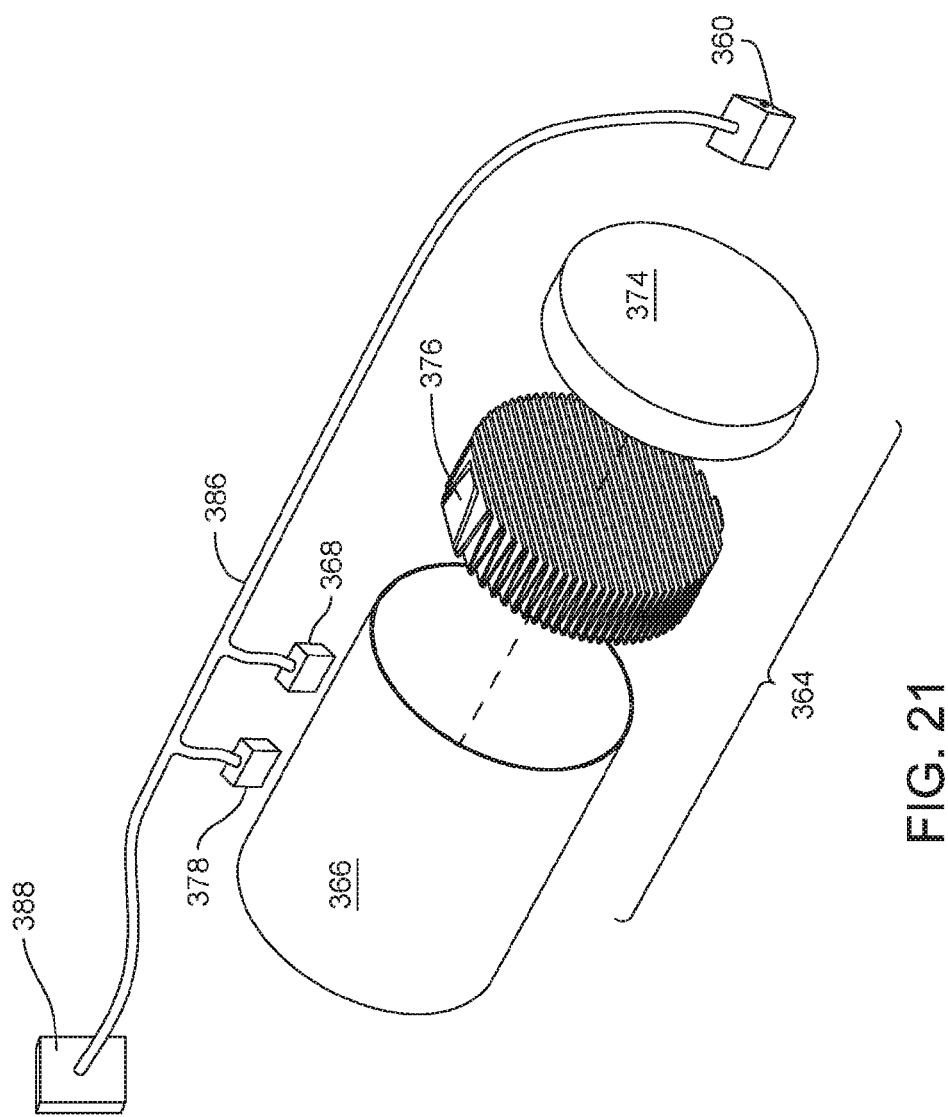
FIG. 21 is an exploded view of the filter assembly internal to the filter, the filter assembly including the wire harness.

The filter assembly 364, as seen in FIG. 21, includes a hollow cylindrical shell 366. The shell 366 is dimensioned to extend between the face plate 330 and the housing end plate 324. Shell 366 thus extends over coupler body 338. The extension of fitting lumen 346 opens into shell 366. One or more filter elements 374 and 376 are disposed in shell 366. The structure and number of the filter elements is not part of the present invention.

Two sensor heads, head 368 and head 378, are mounted in the shell 366. Sensor head 368 is located in the shell so as to monitor the air flow out of the fitting lumen 346 into the filter elements. Sensor head 378 is mounted to the shell so as to monitor the air flow out of the filter elements 374 and 376 that is discharged through the opening 326 in the rear end of the filter housing. While not apparent from the drawings, each sensor head 368 and 378 may be seated in a cutout formed in the shell 366.

Each sensor head 368 and 378 includes two sensor elements, shown as block components in FIG. 8A. Sensor head 368 includes a smoke sensor 370 and a pressure sensor 372. Sensor head 378 includes a smoke sensor 380 and a pressure sensor 382. The smoke sensors 370 and 380 generate signals representative of the amount smoke, the level of particulates in the air flow that flow by the sensors. In some versions of the invention, sensors 370 and 380 are optical sensors that monitor the optically transparency or optical reflectively of the air stream. Pressure sensors 372 and 382 generate signals representative of the pressure of the air flow to which the sensors are exposed.

A wire harness 386 is also disposed in filter housing 322. The wire harness includes the wires that extend from LED 360 and sensors 370, 372, 380 and 382. The wire harness 386 is located outside of the shell 366. Not shown is opening in the shell through which the wires that extend from LED 360 and sensors 370, 372, 380 and 382 86 extend out of the shell. A plug 388 is attached to the proximal end of the wire harness 386, the end of the harness spaced from the smoke filter face plate. Plug 388 is mounted in the opening 327 that is formed in the housing end plate 324. It should be appreciated that when smoke filter 320 is fitted in receptacle 180, plug 388 sets in socket 186.

VI. Smoke Line

One possible smoke line 402 of this invention is depicted in FIG. 22. For the purposes of this description of the invention, the smoke line 402 is similar to the previously described suction line 250. Thus, smoke line 402 includes a proximal fitting 404, a flexible tube 406 and a distal fitting 412. The proximal and distal fittings 404 and 412, respectively, are essentially identical structure to the previously described suction line fitting 252. The tube 406 may be substantially identical to tube 280. Tube 406 thus includes a lumen 408 through which the smoke laden air is drawn. Embedded in the body of tube 406 is a fiber optic core 410. A difference between the suction tube and the smoke line is that the components forming the smoke tube 402 may be smaller or larger in size than the components forming the suction tube 250.

VII. Smoke Pen

Figure 23:
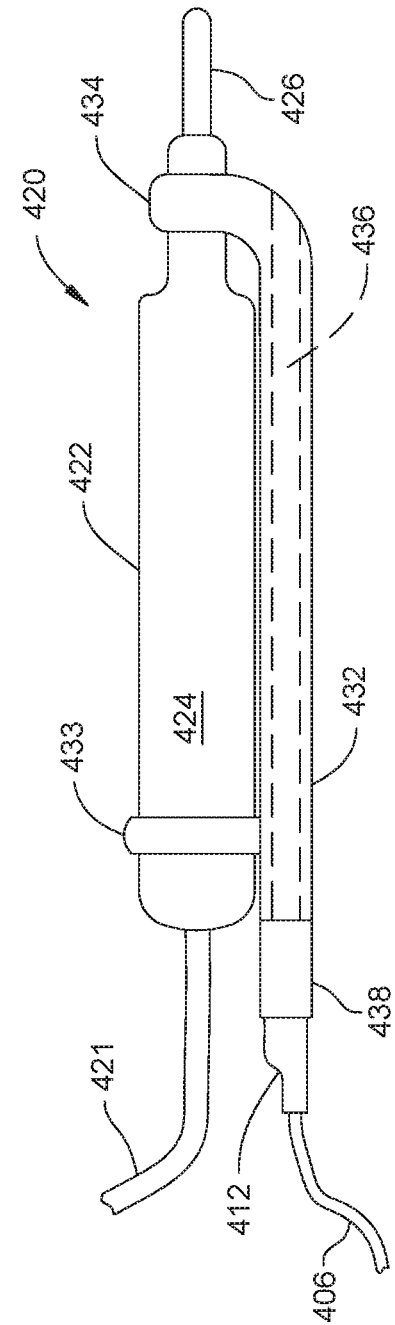
FIG. 23 is a side view of a smoke pen of this invention.

One smoke pen 420 of this invention is shown in FIG. 23. Smoke pen 420 consists of an electrosurgical tool 422 to which a boot 432 is removably attached. Tool 422 includes a handle 424 from which a conductive tip 426 extends. A current is applied to tip 426 so as to result in the heating of the tissue to which the tip is applied. The tissue is heated so as to cut or cauterized the tissue. For the purposes of completeness, the cable 421 over which current is sourced to tool 422 is shown connected to the proximal end of the tool.

Boot 432 is formed of flexible material and is generally elongated in shape. This material is also translucent. Boot 432 is fitted to tool 422. The exact means by which the boot 432 is fitted to tool 422 is not part of the present invention. However, for purposes of illustration it is seen that the boot has a collar 433 adjacent the proximal end of the boot and a collar 434 adjacent the distal end of the boot. Collar 433 is disposed over the proximal end of the body of the handle 422. Collar 434 is disposed over the distal end of the tool handle 422. A lumen 436, shown in phantom, extends longitudinally, proximally to distally through the boot. The lumen 436 is open at the distal end of the boot. A coupling 438 is attached to the proximal end of the boot. The coupling is configured to receive the distal fitting 412 integral with smoke tube 402. When the smoke tube 402 is attached to coupling 438, the fiber optic core internal to the distal fitting 412 abuts boot 432.

VIII. Operation

Unit 40 of this invention is prepared for use by placing a manifold 220 in the receiver 54 or 56 associated with the canister 46 or 48 into which the waste is to be collected. To perform this process, the manifold tabs 234 and 235 are aligned so that each tab seats in the appropriate lock ring slot 160 or 162. This alignment ensures that the manifold outlet opening 224 is in registration over the boss 146 integral with the receiver valve plate. As a result of the insertion of the manifold in the receiver shell void space 132, boss 146 extends through opening 224 into the void space internal to the manifold.

The manifold 220, while in the receiver shell 130, is then rotated. This rotation has two results. First this rotation is transferred through valve plate boss 146 to the valve plate to cause a like rotation of the valve plate 142. The rotation of the valve plate results in a shift of the rotational position of the valve plate so the plate moves from the closed position to the open position. Secondly, this rotation of the manifold 220 places each of manifold openings 243 in registration with a separate one of the ports that extend from the light ring bores 176. More particularly each port is visible through portion of the associated hole 242 located slightly inward of the section of the manifold rim 240 that defines the outer perimeter of the hole. Also, it should be understood that both the manifold head 236 and rim 240 are spaced forward of the receiver light ring 170.

One or more suction tubes 250 is then attached to the manifold 220. A line 250 is attached to the manifold by seating the fitting sleeve 253 over a fitting 241 and seating the fitting fin 256 in the adjacent manifold hollow 242. In this process, the webs 244 defining hollow 242 seat in the sections of the fitting notch 254 on either side of the fin 256. The fitting foot 258 seats in associated opening 243 formed in the manifold 220. Owing to the dimensioning of the components of this invention, during this insertion process, the tapered surface of the fitting tab 260 is pressed against the underlying section of the manifold rim 240 that defines the through openings. The fitting fin 256 is able to flex relative to the sleeve 253. This means that, as the fitting is continued to be coupled to the manifold 220, tab 260 passes through the hole 242. Once the tab 260 extends through the hole 242, owing to the elastic nature of the material forming the fitting 252, the tab 260 flexes into a position in which the tab is disposed against the proximal facing surface of manifold web 240. This component-against-component abutment prevents the pulling on the suction line 250 from unintentionally disconnecting the line from the manifold 220.

A further result of the coupling of fitting 252 to the manifold receiver is that, owing to the dimensioning of the components, the fitting 252 seats against the receiver light ring 170. The components are further arranged so this places the proximal end face of fiber optic core 276 in registration with the adjacent port that extends from the light ring bore 176.

Another result of the seating of the suction tube fitting 252 to the receiver is the pressing of the fitting ribs 270 against the manifold fitting 241. The abutment of these components forms a seal between these components.

The distal suction tube fitting 252 is attached to coupling 302 integral with the suction applicator 290. This results in the connecting of the applicator suction lumen 304 to the suction line tube 280. This coupling further results in the abutment of the fiber optic core 276 internal to the distal fitting 252 connecting to the handpiece fiber optic core 304. The seating of the tab 260 of the distal section tube fitting 252 against a complementary tab internal to the coupling 302 releasably holds the suction line 250 to the suction applicator 290.

If the procedure is one in which smoke will also be generated, unit 50 is configured to function as the unit through which the smoke is drawn away from the patient. As part of this process a smoke filter 320 is seated in receptacle 180. This process results in filter plug 388 connecting to receptacle socket 186. Typically, the smoke filter 320 is always attached to unit 40. This is because filter 320 can often be used to filter the smoke drawn away from a patient for a number of different procedures. Since the smoke filter is not in the sterile field around the patient, the filter can be used with multiple patients.

Smoke line proximal fitting 404 is fitted to coupling 336 integral with the smoke filter 320. The seating of the tab integral with the proximal fitting 404 behind tab 350 internal to coupling 330 releasably holds the smoke line 402 to the smoke filter 320. In the event the smoke line 402 is pulled away from the filter, the tab-against-tab abutment prevents the unintended disconnection of the smoke line from the filter.

Figure 24A:
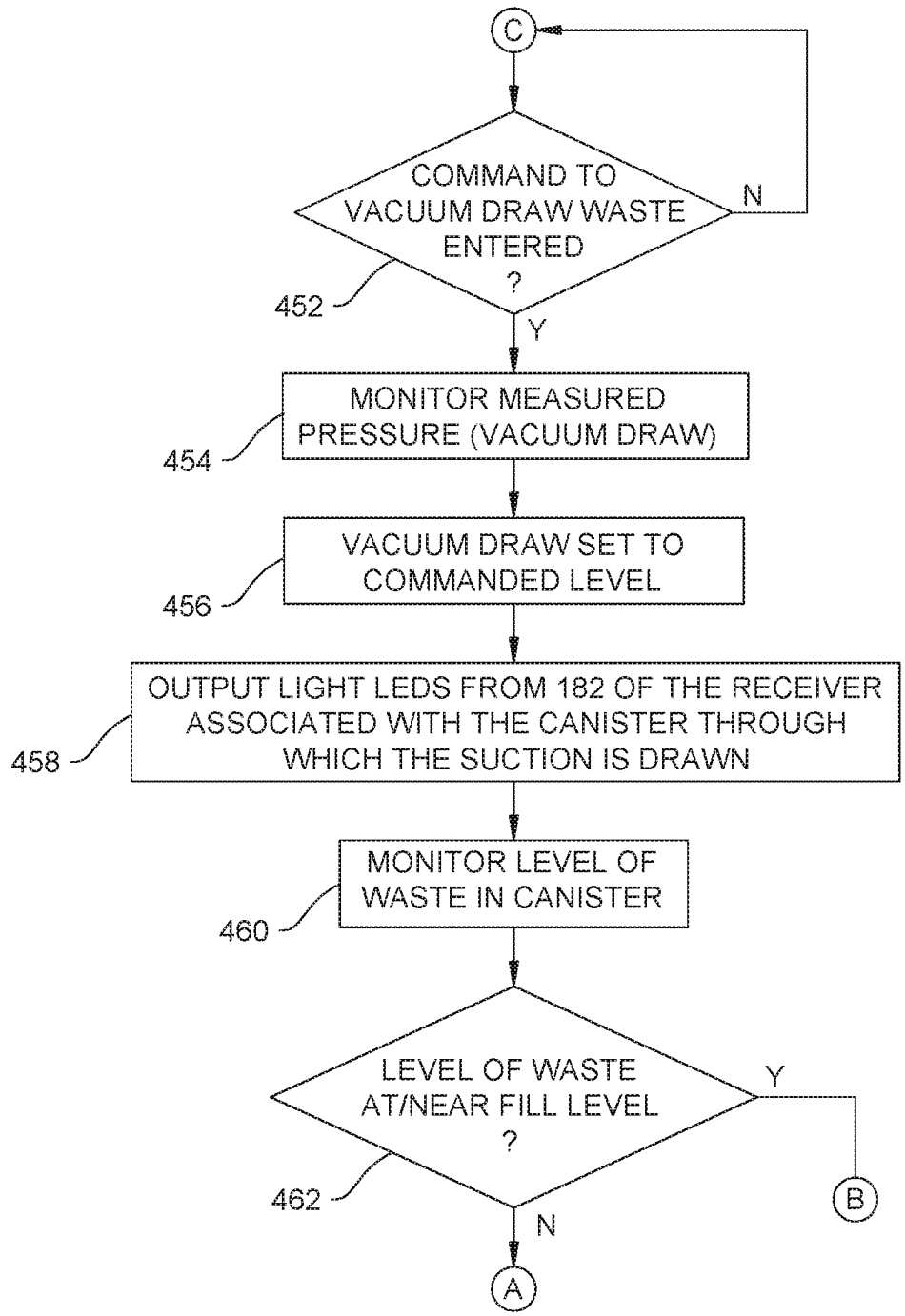
FIGS. 24A and 24B, when assembled together, form a flow chart of the steps by which this invention draws waste away from a surgical site and displays information about this process.

Once the unit 40 is ready for use, the unit is used to draw liquid/semi-liquid waste away from the surgical site or to draw smoke away from the site. Step 452 of FIG. 24A represents the entry of a command through I/O display 106 to draw waste into one of the canisters 46 or 48. Integral with this command are the instructions that the suction draw should be at a specific vacuum level. The suction draw command, it is understood is entered by rotating the knob 113 or 114 associated with the canister 46 or 48, to which the suction line is presented. The associated image 111 provides an indication of the level of the commanded suction draw. In a step 454, processor 196 monitors the pressure, the vacuum level, of the canister 46 or 48 or the attached suction line. This monitoring is performed by monitoring the vacuum level signals generated by the pressure sensor 202 or 204 associated with the canister 46 or 48, respectively, the vacuum of which is being controlled.

In a step 456, processor 192 commands the vacuum regulator to set the vacuum draw to the commanded vacuum level. This step 456 is performed by comparing the measured vacuum draw to the commanded vacuum draw. Based on this comparison, the vacuum regulator 74 may be commanded to selectively connect the appropriate canister 46 or 48 to either the suction pump 76; atmosphere; or neither the pump nor atmosphere.

Figure 24B:
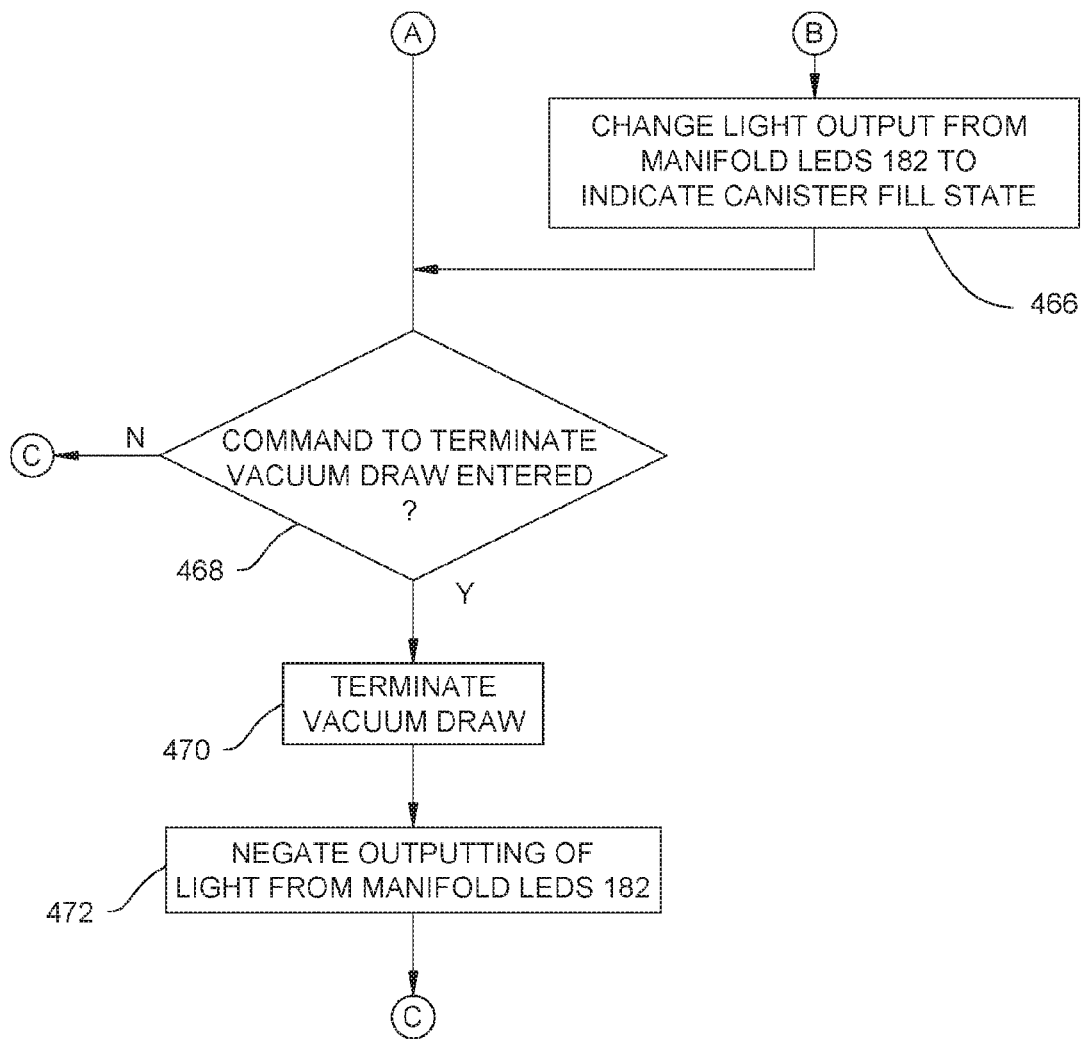

The processor continually compares the measured vacuum draw to the commanded vacuum draw to ensure that the measured draw is as close as possible to the commanded vacuum draw. In FIGS. 24A and 24B, this is represented by the loop back from step 468 to step 452. The loop is shown as starting at step 452 because during the course of the procedure the practitioner may reset the level of the commanded vacuum draw. Thus, the executions of step 452 after the first positive execution of this step are understood to mean the entry of commands to reset the level of the vacuum drawn.

Also, based on the measured vacuum level, processor 196 causes the selectively emission of light by the LEDs 182 associated with the canister into which the waste is being drawn, step 458. Generally, the color of the emitted light is a function of measured vacuum level. For example, in some versions of the invention, processor 192 may cause LED 182 to light in the green wavelengths when a low suction is drawn, a suction generally less than 80 mmHg. As the level of suction increases above 80 mmHg, processor 192 causes the LED 182 to emit light in the wavelengths that are generally perceived as yellow. As the sensed vacuum draw meets and exceed a high level, for purposes of example, 120 mmHg, the processor 192 causes the LED 182 to emit light that is perceived as orange in color.

The light emitted by the LED 182 is transmitted through the adjacent bore 176 in the light ring 170. The fitting foot 258 is located adjacent the opening end of the bore 176. Since the exposed end of the fiber optic core 276 is disposed in the foot 258, the light emitted from the LED 182 enters the fiber optic core 276. From fiber optic core 276 the light travels through core 282 integral with tube 280. From fiber optic core 282 the light travels through the fiber optic core 276 integral with the distal fitting 252. From fiber optic core 276 the light flows through the fiber optic core 304 integral with the handpiece of the suction applicator 290. The light is emitted through translucent block 296. This makes it possible for the practitioner, without diverting his/her eyes from the suction applicator 290, to see a visual indication of the level of the vacuum draw through the applicator.

During the procedure the level of the vacuum draw through the suction applicator 290 may change. As represented by the loop back, unit processor 192 repetitively executes steps 456 and 458. Thus the light indicative of the vacuum draw that the practitioner sees changes as a function of changes in the level of this vacuum draw.

As represented by step 460, processor 192 also monitors the level of the waste collected in the canisters 46 and 48. This monitoring is performed by monitoring the signals generated by the level sensors 206 and 208. Based on this monitoring, in a step 462, the processor determines whether or not the volume of waste collected in a canister is approaching a level at which the canister will soon be filled. In the event the canister level signal indicates canister 46 or 48 is in this state, the processor, as represented by step 464, asserts signals that cause the LED 182 associated with the canister 46 or 48 to output a pattern of light that serves as an indication that the canister is in this state. For example, in some versions of the invention, processor 192 normally causes the steady emission of light at a constant color to be emitted when the canister is less than full. If step 464 is executed, the processor 192 causes the LED 182 to emit the same color and to do so in a flashing on/off/on/off pattern. This change in the displayed light gives the personnel notice regarding the fill state of canister 46 or 48. This gives the personnel the ability to plan the interruption of the procedure so the canister can be emptied at a time when this act is minimally disruptive to the procedure.

Unit 40 of this invention continually draws a vacuum through the suction line, and outputs light representative of the level of the vacuum draw until the practitioner no longer requires the vacuum. In FIG. 24B this is represented by decision step 468. Step 468 represents the detection by the processor 192 that a command has been entered to terminate the drawing of waste into the canister 46 or 48. Once the processor 192 determines that this command has been entered, the process terminates the vacuum draw, step 470. Step 470 may be executed by having the vacuum regulator connect the appropriate canister to atmosphere.

In a step 472 the processor 192 negates the output of light from the LED 182 of the receiver associated with the canister 46 or 48 through which the suction is drawn. The resultant negation of light from the suction tube 280 and suction applicator 290 provide notice to the personnel performing the procedure that a vacuum is no longer being drawn through these components.

Processor 192 then waits to receive a new command that suction should be drawn into the canister 46 or 48, return to step 452.

Once the procedure is completed, the suction tube 250 is disconnected from both the suction applicator 290 and the manifold 220. To so disconnect the tube 250, force is applied to the proximal fitting 252 to overcome the resistance of the manifold rim 240 blocking the outward movement of tab 260. This results in the proximal tab 260 moving inwardly from the component against which the tab abuts. The distal tab 260 abuts a similar surface integral with applicator coupling 302. Once the tab 260 clears the component against which the tab abuts, the fitting can be pulled out of the manifold or applicator to which the fitting is coupled. The manifold is removed from the receiver 54 or 56 to which the manifold is attached by rotating the manifold. The manifold is rotated until the manifold tabs 234 and 235 go into registration with the distal sections of the corresponding slots 160 and 162, respectively. This rotation closes the valve internal to the manifold. The manifold 220 is then withdrawn from the receiver 54 or 56.

Smoke line 402 is disconnected from the smoke filter 320 and smoke pen 420 in a manner similar to which the suction line 250 is disconnected from the manifold 220 and the suction applicator 290.

Figure 25A:
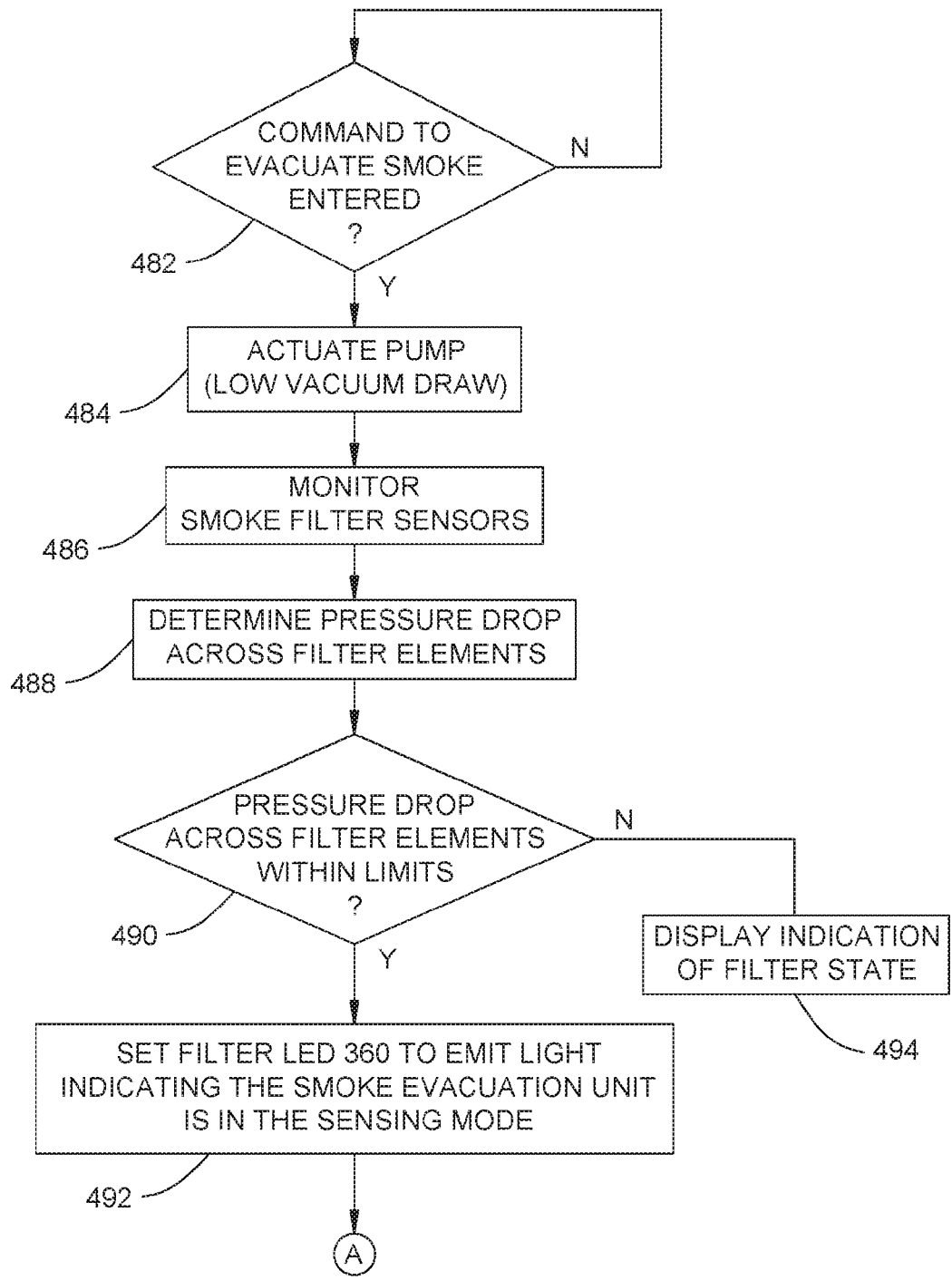
FIG. 25A-25C, when assembled together, forms a flow chart of the steps by which this invention evacuates smoke away from a surgical site and displays information about this process.
Figure 25B:
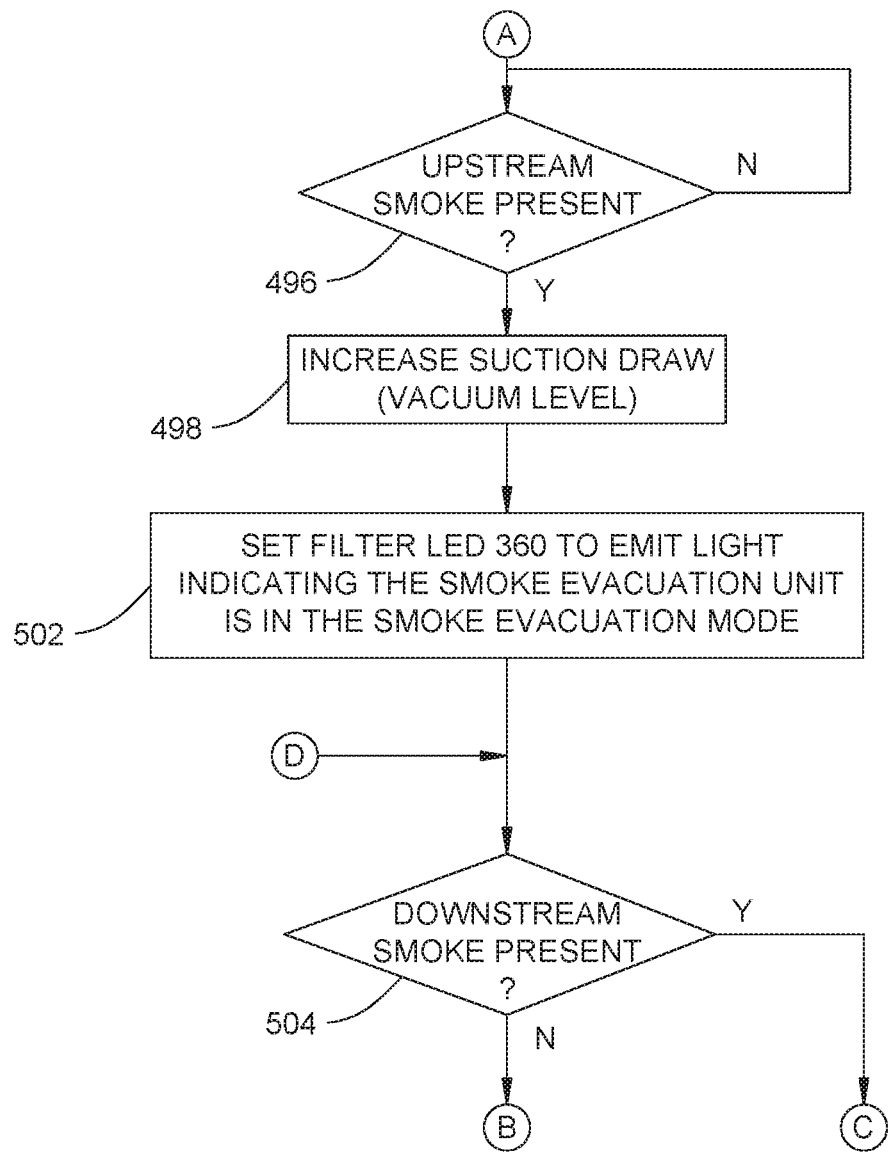
Figure 25C:
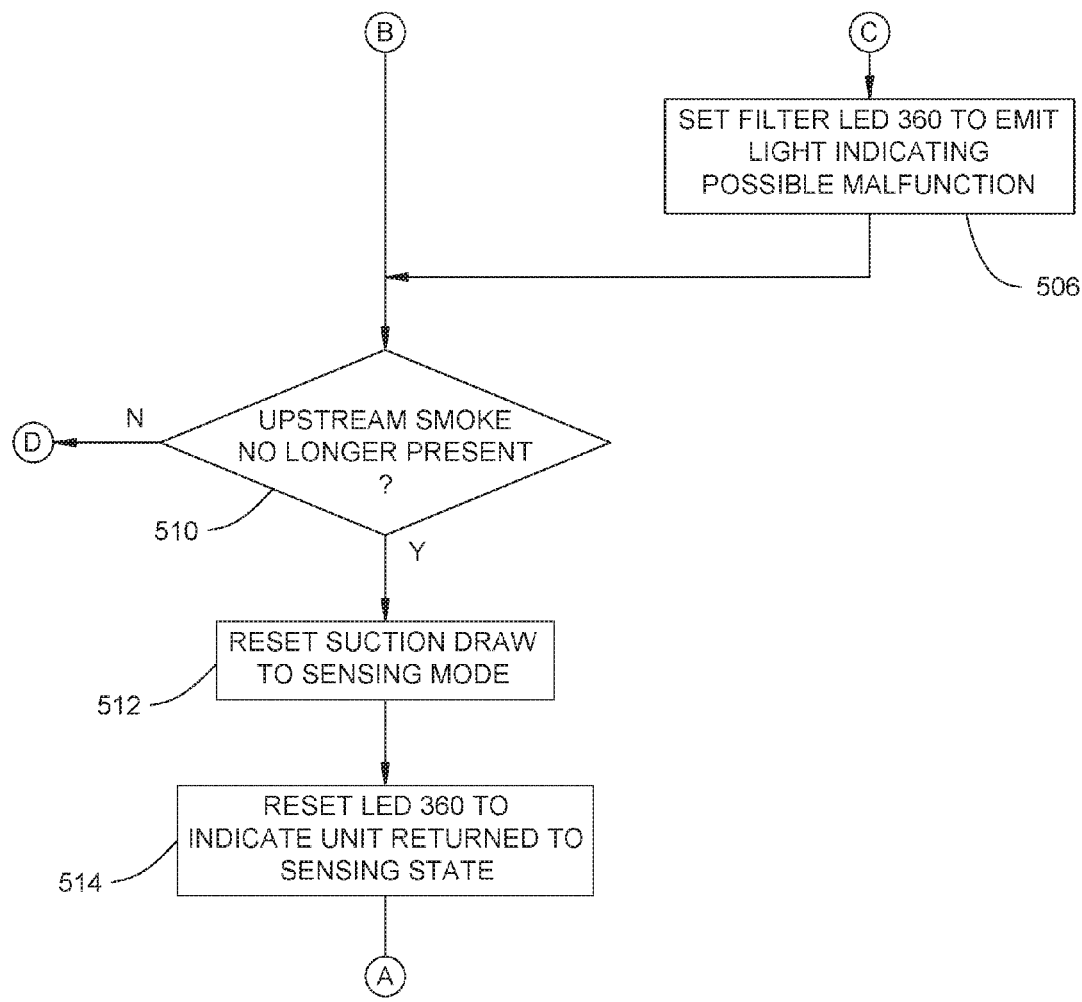

Either simultaneously with or independently from the collection of liquid waste, unit 40 may be set to evacuate smoke. As represented by step 482 of FIG. 25A, this process starts with the entry of a command through I/O display 106 to the processor 192. In response to this command, processor 192, in a step 484, actuates the motor 81 connected to the pump 82 so that the motor runs in a low speed mode. As long as the unit 40 is set to evacuate smoke, the processor continually monitors the signals output by sensors 370, 372 380 and 382. This is represented once by step 486.

In a step 488 the processor determines the pressure drop across the filter elements 374 and 376. Step 488 is executed by monitoring the signals representative of pressure upstream and downstream from the filter elements as indicated by the signals output from sensors 372 and 382, respectfully. Step 490 represents the evaluation if this pressure drop is above a predetermined level. Processor 192 interprets the pressure drop being below the predetermined level as an indication that the filter elements are not clogged with filtered particles and smoke evacuator 80 can efficiently evacuate smoke. Should the processor make this determination, the processor in a step 492, causes LED 360 to emit a specific color of light or a specific pattern of light. This light is transmitted through the fiber optic cores integral with smoke line 402 to the smoke pen 420. The color of the light emitted by the smoke pen 420 provides a visual display to the practitioner that the smoke evacuator is actuated and the pressure drop across the filter elements is acceptable.

Alternatively, in step 490, the signals from pressure sensors 372 and 382 may indicate that the pressure drop across the filter elements 374 and 376 is above the predetermined level. The processor 192 interprets this determination as indicating that the filter elements may be so clogged with filtrate that the smoke evacuator may no longer be able to operate efficiently. If processor 192 makes this determination, in a step 494 the processor generates an indication regarding the state of the smoke evacuator. This indication may be presented on the I/O display 106. In addition or alternatively, this indication may be displayed by selectively actuating LED 360. Thus, the LED may be set to emit a specific color light or specific pattern of lights to provide this indication regarding the state of the smoke filter 320. This information regarding the smoke filter 320 serves as a cue to the personnel using the unit 40 that it may be desirable to change the filter.

In step 484, processor 192 set the motor 81 to run at a relatively low rate of speed. This, in turn, results in pump 82 drawing a relatively low vacuum through the smoke pen 420 and smoke line 402 into the smoke filter 320. This vacuum is at a sufficient level to ensure that the mass forming the air stream flowing through the filter is sufficient to cause the detection of smoke by sensor 370.

Step 496 represents the evaluation of the signal output from sensor 370 by the processor 192 to determine if there is an appreciable amount of smoke in the air stream that flowed through the filter assembly. As represented by the loop back representing the continuous execution of step 496, the processor 192 continues to cause the motor 81 to run at a low speed and continues to monitor the signal output from sensor 370.

During the course of the medical or surgical procedure, smoke, particulate matter, may be generated. When the pump is operating at a relatively low suction draw level, only a fraction of the smoke may be drawn into the smoke filter 320. The smoke drawn through the filter when the unit 40 is in this operating state is typically enough to be sensed by sensor 370. When, based on the change in the signal from sensor 370, the processor 192 determines that smoke is present, the processor increases the operating speed of the motor 81. The increase in motor speed, in turn, causes pump 82 to increase the level of the vacuum drawn through the smoke pen 420, collectively these events are represented by step 498. This results in a large fraction of the smoke-laden air being drawn into the unit. The particulate matter forming the smoke is removed from the air stream by the filter elements 374 and 376. Smoke evacuation unit 80 returns to the space in which the procedure is being performed air that is relatively particulate free.

Also as a result of processor 192 determining that the air drawn into the smoke evacuation unit 80 includes detectable smoke, the processor, in step 502, changes the color of the light emitted by LED 360. The resultant change in the light emitted by the smoke pen 420 serves as a visual display to the medical personnel that smoke evacuation unit 420 has transitioned into an active state in which the unit is now evacuating the particulate laden air from the space surrounding the smoke pen 420.

During this part of the procedure, processor 192 monitors the signal output by smoke sensor 380. As represented by step 504, this monitoring is performed to determine whether or not there is detectable smoke downstream from filter elements 374 and 376. Assuming that the smoke filter is properly functioning, there should not be detectable smoke. If the smoke filter is so functioning, the filter proceeds to the below described step 510. There is a possibility that the signal from sensor 380 indicates that there is detectable smoke in the downstream airflow. In step 504, processor 192 interprets receipt of this type of signal as indicating that there may be a malfunction with the smoke filter 320. If this determination is made, in a step 506, the processor sets LED 360 to emit a different color and/or sequence of lights from what was emitted in step 480. The light emitted by the smoke tube 410 and/or smoke pen 420, when in this state serves as an indication that smoke evacuation unit 80 may be malfunctioning. This gives the personnel notice to decide whether or not they want to continue using the smoke evacuator or to attend to the malfunction.

Step 510 represents the continued monitoring of the smoke detected by sensor 370 upstream of the filter elements 374 and 376. As long as there is no change in the signal indicating there is detectable smoke, as represented by the loop back from step 510 to step 504, processor continues to cause a high level vacuum to be drawn and LED 360 to emit light indicating that the smoke evacuation unit 80 is evacuating smoke.

Eventually the portion of the medical/surgical procedure in which the smoke is generated concludes. This results in a drop in the smoke detected by sensor 370. In step 510, the processor 192 interprets the change in the signal from sensor 370 as an indication that, given the absence of smoke, there is no need to draw substantial quantities of air through the smoke evacuation unit 80. Processor 192 resets speed of motor so that the motor operates a low speed. This results in the pump returning to the state in which the pump operates at a relatively low vacuum level and draws a relatively small volume of air into the smoke filter. Collectively these sub-steps are represented by step 512. In a step 514, the processor resets the color and/or pattern of light emitted by LED 360. More particularly, the LED 360 is reset to emit the pattern of light it was set to emit in step 492. Processor continues to reexcute step 496.

Unit 40 of this invention is thus designed to provide medical and surgical personnel using the unit a visual indication of the operating state of the unit by merely looking at the devices that are connected to the unit or the lines 250 or 402 that extend from the devices back to the unit. During a procedure, lines from three different units that draw fluid could be present at the surgical site: lines 250 from canister 46; lines 250 from canister 48; and a line 402 from the smoke evacuator 80. At a given instant, different suctions could be drawn through the lines 250 connected to the canisters 46 and 48 and the smoke evacuator could be active. Unit 40 is configured so that the lights emitted as a result of these different fluid draws are of different color and/or sequence. This gives personnel the opportunity of simply looking at the light emitted by each suction applicator or the smoke pen to determine the fluid draw state of each of these components. This eliminates the need to have an individual turn his/her head away from the procedure in order to view this information on the I/O display.

Still another feature of this invention is that only a small portion of each suction line 250 and of the smoke line 402 is illuminated. The body of the tubes 280 and 406 integral with these lines remains transparent. This allows the medical personnel the ability to inspect the lumens internal to these tubes for clogs. Further, since portions of the lines 250 and 402 are themselves illuminated it allows the medical personnel to be looking at the lines themselves, quickly determine the states of the vacuum draws through these tubes.

Further, in many uses of unit 40 the levels of the suction drawn into canisters 46 and 48 are different. This means that often the light simultaneously emitted through the suction lines 250 connected to these canisters will be of different color or different patterns. This provides the personnel a relatively simple means to determine which line is connected to which canister 46 or 48. Similarly, the light/pattern of light emitted by LED 360 is often different from the light simultaneously emitted by LEDs 182. This means that emitted from the smoke line 402 is different from the light emitted through the suction lines. Again, this simplifies the efforts required to determine if a particular line is connected to one of the waste canisters 46 or 48 or the smoke filter 320.

Further, in order for the personnel to determine the level of the suction draw, all that is necessary to do is perceive the color of the emitted light. This information, the determination of color, is mentally processed faster than providing a text image with the same information. Thus this invention provides a quick means for personnel to rapidly determine approximate suction level without having to engage in significant thought. Providing the information in this form reduces the extent to which the processing of this information interrupts the other mental activities of the person needed this information.

IX. Alternative Suction Tube

Figure 26:
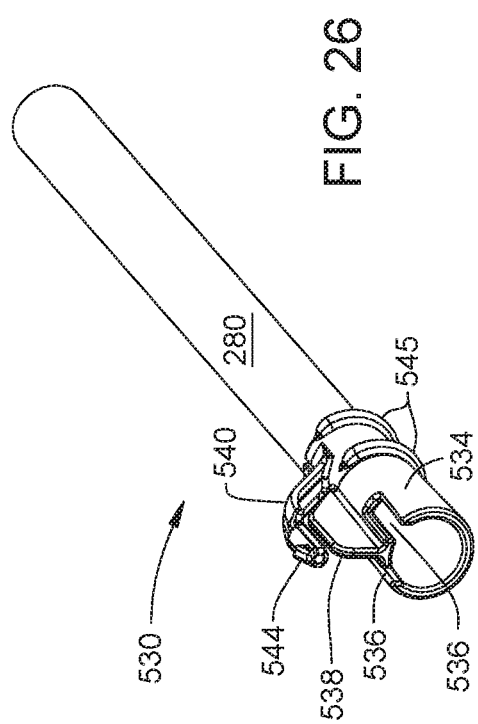
FIG. 26 is a perspective view of the proximal end of an alternative suction line of this invention.
Figure 27:
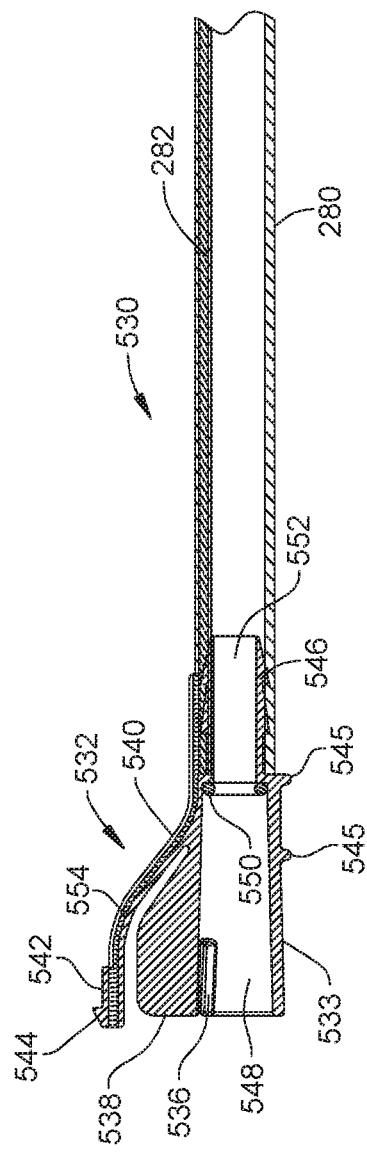
FIG. 27 is a cross sectional view of the proximal end of the suction line of FIG. 26.

FIGS. 26 and 27 illustrate an alternative suction line 530 of this invention. Suction line 530, like suction line 250, is designed for use with manifold 220 and suction applicator 290. The suction line 530 includes the previously described tube 280 with fiber optic core 282. Suction line 530 includes fittings attached to the opposed proximal and distal ends of the tube 280. Only the proximal fitting, fitting 532, is shown, the distal fitting being identical to the proximal fitting.

Fitting 532 is formed from material that is more rigid than the material from which fitting 252 is formed. One material from which fitting 532 can be formed is polypropylene plastic. Fitting 532 is shaped to have a cylindrical sleeve 533. The sleeve 533 has a proximal section, section 534. The sleeve proximal section 534 is formed to have two parallel notches 536 that extend distally forward from the proximal end of the sleeve. A fin 538 extends radially outwardly from sleeve proximal section 534. Fitting 532 is formed so that fin 538 extends outwardly from the arcuate section of sleeve 533 located between notches 536. Above the arcuate section of the sleeve 533, between the notches 536, the fin 538 has a generally constant height. Forward of notches 536, height of the fin decreases extending distally along the sleeve.

The fitting 532 also has a leg 540 that projects outwardly from sleeve 533. Leg 540 extends outwardly from the section of sleeve 533 immediately forward of the location where the fin 538 merges into the sleeve. The leg 540 extends proximally over and spaced outwardly from the 538. Fitting 532 is further formed so the proximal section of the leg, section 542 extends outwardly from the section of the leg immediately forward the section. A foot 544 extends outwardly from the proximal end of leg proximal section 542. Foot 544 has the same geometric shape as tab 260 of fitting 252. Owing to the material from which fitting 532 is formed, leg 540, including foot 544, are able to flex relative inwardly towards fin 538.

Two ribs 545 project partially circumferentially outwardly around the sleeve proximal section 534. Both ribs 545 subtend an arc that extends approximately 270° around the sleeve proximal section 534. The ribs 545 are spaced away from the longitudinal section of the sleeve proximal section from which fin 538 and leg 540 project away from the sleeve 533. The proximal one of the two ribs 545 extends outwardly from the small section of the sleeve proximal section 534 between where fin 538 and leg 540 emerge from the sleeve proximal section 534. The distal one of the two ribs 545 extends outwardly from the distal end of the sleeve proximal section 534. Ribs 545 function as surface discontinuities of the sleeve proximal section 534 that facilitate finger gripping of the sleeve.

Forward of the proximal section 534, the sleeve 533 has a distal section, section 546. Sleeve distal section 546 has a diameter that generally is less than that of the sleeve proximal section 534. Two barbs, (not identified) extend circumferentially around sleeve distal section 546. Collectively, the components forming suction line 530 are dimensioned so that the tube 280 can be press fitted over the sleeve distal section 546 and the barbs facilitate the retaining of the fitting 532 to the tube 280. In FIG. 27 the sections of the barbs that project outwardly from sleeve distal sections 546. This is for ease of illustration only.

Two contiguous bores, bores 548 and 552, collectively form a lumen that extends axially through sleeve 533. The first bore, bore 548, extends distally from the proximal end of the sleeve 533. Notches 536 extend into bore 548. Bore 548 terminates at a location approximately 5 mm forward of where leg 540 merges into the sleeve. The second bore, bore 552, extends forward from the proximal end of bore 552 through the whole of sleeve distal section 546. Bore 552 is smaller in diameter than bore 548. The fitting 532 is formed so that the bore 552 extends through the distal portion of the sleeve, the portion of the sleeve over which tube 280 is fitted. A compressible O-ring 550 is disposed against the annular step internal to the sleeve that defines the transition between bore 548 and bore 552 (step not identified).

A fiber optic core 554 is disposed in fitting 532. Fiber optic core 554 extends from the proximal end of leg 540 through the whole of the leg. The fiber optic core 554 has a distal end face that is exposed in the annular step located around the outside of the sleeve that defines the transitions between sleeve proximal and distal sections 534 and 546, respectively. (Sleeve step not identified). When the suction line 530 is assembled, tube 280 and fitting 532 are oriented relative to each other so that the distal end face of fitting fiber optic core 554 abuts the proximal end face of tube fiber optic core 282.

While not illustrated, the suction line 530 may have a distal end fitting that is essentially identical to the above-described proximal end fitting 532.

Suction line 530 is used in the same general manner in which suction line 250 is used. Once a manifold 250 is attached to one of the receivers 54 or 56, the suction line is fitted to the manifold. The proximal end fitting 532 of the suction line 530 is seated over one of the manifold fittings 241. The manifold fitting 241 seats in the bore 548 internal to the suction tube fitting 530. The O-ring 550 provides a seal between the two fittings 241 and 532. The proximal end of fin 538, the portion of the sleeve 533 from which the fin extends, leg 540 and foot 544 fit in manifold hole 242. More particularly, owing to the flexibility of the leg 540, the portion of the leg from which foot 544 extends passes proximally beyond the manifold rim 240. The proximal end of the leg thus abuts the portion of the receiver light ring 170 in which one of the LEDs 182 is seated. Foot 544 abuts the proximal facing surface of manifold rim 240. This component-against-component abutment prevents the unintended decoupling of suction line 530 from the manifold 220. Any distal end fitting integral with suction line 530 may be attached to a suction applicator 290 in the same general manner in which line 250 is attached to the applicator.

Unit 40 of this invention operates the same way with suction line 530 as the unit operates with suction line 250. When processor 192 determines that the LEDs 182 integral with the receiver 54 or 56 to which the line 530 is attached should emit light, the processor generates instructions causing the LED to emit light at a specific color and/or in a specific pattern. The light emitted by an LED 182 will be transmitted through the fitting fiber optic core 554. From the fitting fiber optic core 554, the light will be transmitted through the tube fiber optic core 282. If a suction applicator 290 capable of emitting light is attached to the distal end of the suction line 530, the light will be visible from the light emitting components of the suction applicator.

A benefit of suction line 530 is that the rigid nature of leg 540 can provides a secure coupling of the line to manifold 220.

X. Lighted Manifold

A manifold receiver 570 that can be integrated into a first alternative unit of this invention is now described by initial reference to FIG. 28. Manifold receiver 570 does not emit light that is transmitted over a fiber optic core integral with the suction line that extends from the receiver. Instead, manifold receiver 570 emits light into the manifold 610 attached to the receiver. This light is emitted, displayed, by the manifold.

Figure 30:
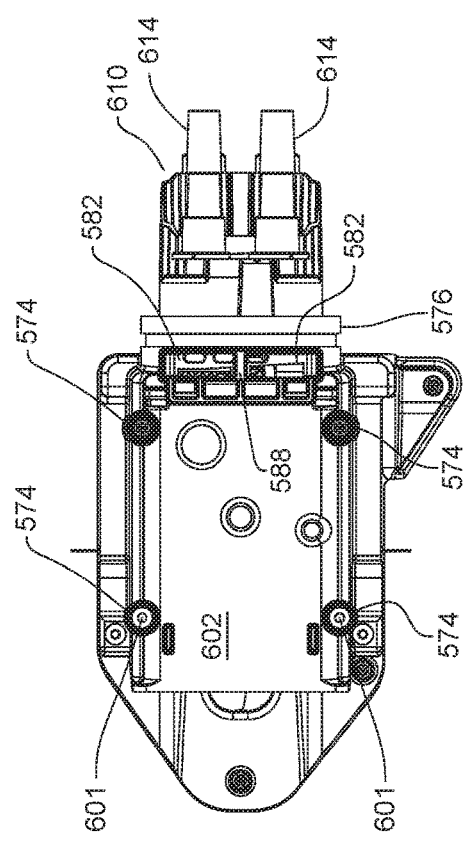
FIG. 30 is a top plan view of the manifold receiver of FIG. 28 with the manifold receiver removed.

Manifold receiver 570 includes a shell 572, seen best in FIGS. 29 and 30. Shell 572 has the same general shape and performs the same basic function as the shells 130 of manifold receivers 54 and 56. Specifically, the shell 572 is dimensioned to receive a manifold 610. Also, while not illustrated, the shell 572 and supporting components form a conduit that provide a fluid communication path to the canister 46 or 48 to which the manifold is mounted. Internal to the shell 572 is a valve (not illustrated) that selectively opens/closes the port into the conduit as a function of whether or not a manifold 610 is seated in the shell.

Formed integral with shell 572 are four posts 574. Two posts 574 extend upwardly from the opposed sides of the shell 572 adjacent the proximal end of the shell. Two posts 574 extend upwardly from the opposed sides of the shell adjacent the distal end of the shell. Posts 574 project above shell 572.

A lock ring 576 extends forward from the open distal end of shell 572. The lock ring 576 is formed so as to have slots 578 and 580 that project radially outwardly from the center opening of the ring through which the manifold is inserted into the receiver 570. Slots 578 and 580 are analogues in shape and function to slots 160 and 162 integral with manifold receivers 54 and 56. Lock ring 576 is further formed so as to have two openings, openings 582, that are located proximal to the distal front face of the ring. The lock ring 576 is formed so that openings 582 extend into the center opening that extends axially through the ring. Collectively the components forming receiver 570 are constructed so that when the receiver is assembled together, openings 582 extend downwardly from the top of the receiver into the lock ring center opening.

A light tube 586 is disposed over lock ring 576. The light tube 586 is in the form of a hollow structure that, in cross section, is generally in the form of a rectangle with rounded corners. The bottom end of the light tube 586 is arcuate in shape to facilitate the seating of this end of the tube over the lock ring. Light tube 586 is further formed so that the top of the tube projects a short distance, approximately 2 mm, above the top of shell 572. A web 588 extends laterally across the minor axis of the light tube. The web 588 thus divides the hollow void internal to the tube into two channels 590. In some versions of the invention, the light tube is mounted to the below discussed circuit board. When receiver 570 is assembled, each channel 590 opens into one of the openings 582 formed in the lock ring. In some versions of the invention, the inner surfaces of the light tube 586 that forms the perimeter of the channels 590 are formed from optically reflective material.

A lattice structure 592 is shown over shell 572 immediately proximal to the light tube 586. Lattice structure 592 is not part of the present invention.

Manifold receiver 570 includes a circuit board 602. The circuit board 602 is mounted to posts 574 so as to be located above shell 572. Fasteners 601 (only two identified) that are disposed over the circuit board 602 and extend into the posts 572 to hold the circuit board to the posts 574.

Figure 31:
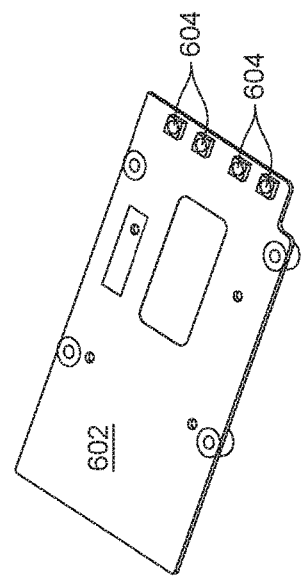
FIG. 31 is a perspective view of the portion of the surface of the circuit board of the manifold receiver of FIG. 28 to which the LEDs are mounted.

Four LEDs 604, seen in FIG. 31, are mounted to the underside of circuit board 602, the side of the board that faces the shell 572. The components forming the receiver 570 are constructed so that when the receiver is assembled two LEDs 604 seat in each of the channels 590 internal to the light tube 586. In this version of the invention, LEDs 604 take the place of LEDs 182. The on/off state as well as the wavelengths of the light emitted by the LEDs 604 are thus controlled by signals asserted by processor 192, connections not shown.

The manifold 610 that fits in receiver 570 has the same basic structure as previously described manifold 220. A difference between these two manifolds 220 and 610 is that the manifold 610 is not provided with the geometric features for receiving one of the described suction line fittings, fittings 252 and 532. Instead manifold 610 includes a cap 612 from which tube like fittings 614 extend proximally forward. Fittings are designed so that a conventional suction tube can be manually press fit over the fittings. Still another feature of manifold 610 is that cap 612 is formed from a translucent material such as polypropylene.

A unit of this invention is prepared for use by inserting the manifold 610 in the receiver 570. If the unit includes the plural canisters, then there is typically a receiver 570 associated with each canister. A manifold 610 is fitted to each receiver if waste is to be drawn into the separate canisters. The proximal end of a conventional suction tube is fitted over one of the manifold fittings 614. The distal end of this tube is connected to a conventional suction applicator. This is a suction applicator that typically does not have a translucent component through which light transmitted over the suction line is transmitted.

A unit with receiver/receivers 570 and manifold/manifolds 610 operates in the same general means by which the previously described versions of the invention operate. Processor 192 monitors the operating state of the waste collection unit. Based on the state in which the unit is in, the processor 192 generates the signals that cause LEDs 604 to emit light at the appropriate wavelength and/or the appropriate pattern. The light is emitted through the light channels 590 and lock ring openings 582 to the cap 612 of the manifold 610 seated in the receiver. Owing to the translucent nature of the material forming the manifold cap, the cap emits the light output by the LEDs 604.

This version of the invention is thus designed so that personnel using the unit can with a simple glance at the manifold determine the operating state of the unit based on the color of the manifold. The personnel do not have to look at the display to obtain this information. It is further feature of this invention, is that the invention can be used with a conventional suction tube. This need to provide a suction tube specifically designed for use with this invention is eliminated.

XI. Lighted Manifold Receiver

Figure 34:
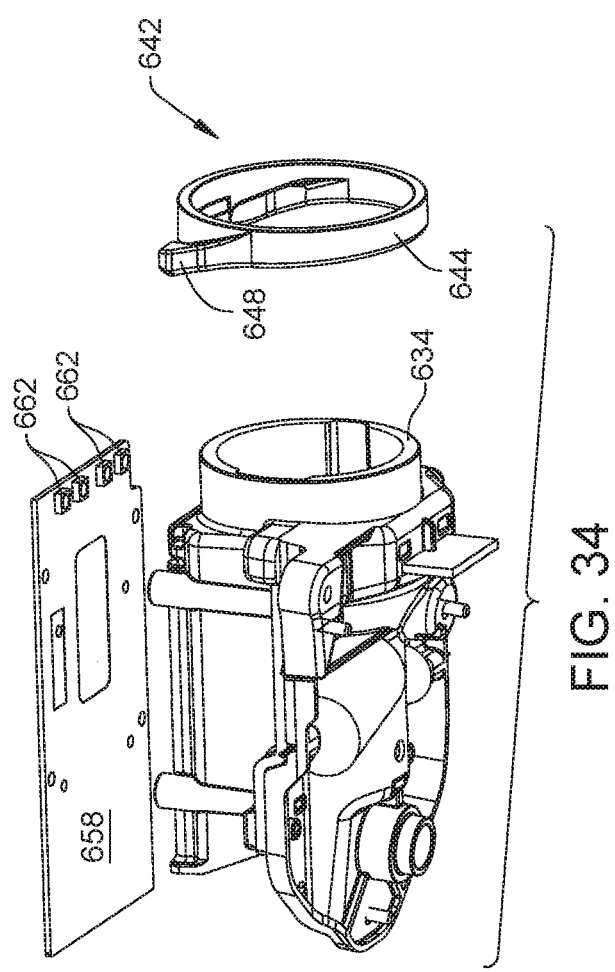
FIG. 34 is an exploded view of the manifold receiver of FIG. 32 depicting the bottom located components of the receiver.

FIGS. 32-34 depict the manifold receiver 630 that can be integrated into a second alternative unit of this invention. Manifold receiver 630 includes a shell 632. Shell 632 is similar in shape and function to previously described shell 572. Integral with shell 632 and extending forward from the open end of the shell is the lock ring 634. Lock ring 634 has the same general shape and has the same general function as lock ring 158.

A light ring 642 is fitted over the outer circular surface of lock ring 634. Light ring 642 is formed from a transparent material such as an acrylic plastic. The light ring 642 has a main body 644 that is generally O-shaped. A head 646 formed integrally with the main body 644 extends upwardly from the main body. The light ring 642 is also formed so as to have two arms 648 that are also formed integrally with the main body 644. The arms 648 are located on the opposed sides of the head 646 and like the head, extend upwardly from the main body 644. The light ring 642 is further formed so that the top surfaces of the head 646 and arms 648 of the ring are essentially coplanar.

A circuit board 658 is secured over the shell 632. Not shown are the fasteners that secure the circuit board 658 to the posts integral with the shell (posts not identified). The circuit board 658 is dimensioned to extend over the head 646 and arms 648 of the light ring 642.

Four LEDs 662 are mounted to the undersurface of circuit board 658, the surface of the circuit board directed towards shell 632. Two of the LEDs 662 are positioned so that the light emitted by these LEDs is directed into the head 646 integral with the light ring 642. The remaining two LEDs 662, the outer of the two LEDs 662, are positioned so the light emitted by each of these LEDs is directed into a separate one of the arms 648 integral with the light ring 642. The LEDs 662, like the previously described LEDs 182, are capable of emitting light at different colors. While not shown it should be understood that the LEDs 662 are connected to processor 192. In versions of the invention that include manifold receiver 630, the processor 192 controls the on/off state of the LEDs 662 as well as which color they emit. This control is the same general control the processor asserts in versions of the invention that include LEDs 182.

A version of the invention that includes the receiver 630 or plural receivers 630 if there are plural canisters, operates in the same general manner in which the previously described versions of the invention operate. The processor 192 monitors signals that indicate the operating states of the various components of this invention. Based on these signals the processor determines the operating state of the unit. Based on this determination, the processor, if appropriate, asserts signals that cause the LEDs 662 to emit light representative of the particular operating state. This light emitted by the LEDs 662 is emitted into the light ring 642. Owing to the optical properties of the light ring 642, the light ring emits this light. Thus, in this version of the invention, the medical personnel by a simple glance to the manifold receiver can determine fundamental information about the operating state of the unit.

A benefit of this version of the invention that include one or more manifold receivers 630 is the color of the light viewed by the personnel using the system is not affected by the color of the waste being drawn into the unit.

Further like the other versions of the invention, the component through which the light is emitted, light ring 642, is separate from the display. The light ring 642 is in close proximity to the fittings 641 to which the suction lines are attached. Thus, like the other versions of the invention, in order for medical personnel to determine the suction draw, there is no need to review the image 112 presented on the display 106. Instead, all that is necessary is look to where the suction line 250 is connected to the waste collection unit. In close proximity to this point, the color of the light emitted by ring 642 provides an means to perceive this information without having to engage in significant mental processing of the viewed scene.

XII. Second, Third, Fourth and Fifth Alternative Suction Lines

FIGS. 35A and 35B depict the distal end of a second alternative suction line 680 of this invention. The proximal end of suction tube 680 as well as the proximal ends of the below described third alternative suction tube 702, fourth alternative suction tube line 720 and fifth alternative suction line 740 can include one of the previously describing proximal end fittings 252 or 532 from which a suction tube extends.

Suction line 680 is constructed so that suction tube 280 extends from the proximal end fitting. The distal end of suction tube 280 is attached to a distal end fitting 682, sometimes called a cuff. Fitting 682 is formed from a flexible opaque material such as a colored silicone rubber. The fitting 682 is shaped to have a tubular stem 684 or barb that forms the proximal section of the fitting. The components forming suction line 680 are constructed so that stem 684 can tightly seat in the open distal end of the lumen internal to suction tube 280. Extending forward from stem 684, fitting 682 has a head 686. The head 686, which is also generally tubularly shaped, has inner and outer diameters that are larger than the corresponding diameters of stem 684. Fitting 682 is further formed so that at the proximal end of the head 688, a ring shaped notch 688 extends inwardly from where the stem 684 extends proximally from the head. The distal end of suction tube 280 is seated in the notch 688.

Two ribs 690 extend circumferentially outwardly around the outer surface of head 686. Ribs 690 facilitate the finger and thumb holding of fitting 682. The fitting 682 is further formed to have a lip 692 that projects radially outwardly and circumferentially around the open distal end of head 686. The below described fittings 708, 722 and 724 have ribs identical to ribs 690 and lips 692.

Two lumens form a through bore that extends between the opposed proximal and distal ends of the fitting 682. A first one of the lumens, lumen 694 extends through the stem 684 and the portion of the head 686 to which the stem opens. Lumen 694 opens into the larger diameter lumen 695. The lumen 695 extends through to and opens outwardly from the distal end of head 686. Two parallel spaced apart ribs 696 extend inwardly from the inner wall of the fitting head 686 that defines lumen 695. Ribs 696 are also present in the lumens of the below described fittings 708, 722 and 724.

The fitting 682 of this invention is designed for attachment to a conventional suction applicator. A conventional suction application is, for the purposes of this invention, a suction applicator that does not have components through which the light transmitted through the suction line 680 is emitted. This type of suction applicator has a fitting designed to snuggly fit in lumen 695 internal to the fitting head 686. When the suction applicator is so coupled to suction line 680, ribs 696 provide a substantially air-tight seal between the suction line fitting 682 and the suction applicator fitting.

While not illustrated, it should be understood that in some versions of the invention the section of fiber optic core 282 that extends from 1 to 3 cm proximally from fitting 682 may be provided with a roughened surface. The roughen nature of this surface ensures that the light transmitted through the core 682 will be emitted outwardly through this section of the core.

When a conventional suction applicator is attached to waste collection unit 40 of this invention with suction line 680, the assembly is used in the same generally manner as the previous described versions of the invention. Based on the processor 192 determining that the unit is in a defined operating state, the processor causes the LEDs 182 of the manifold receiver to which the suction line 680 is connected to emit a specific color or pattern of light. The light is emitted through the fiber optic core 282 embedded in suction tube 280. Thus, instead of having to look at the display 106, the persons performing the procedure only have to determine the color of the fiber optic core 282 to determine the operating state of the suction line 680 and the attached suction applicator.

The third alternative suction line, line 702, now described by reference to FIGS. 36A and 36B, is an alternative to suction line 680. Suction line 702 includes a suction tube 280a that extends distally forward from the proximal end fitting. Suction tube 280a is substantially identical to suction tube 280. A difference in the suction tubes is that suction tube 280 includes fiber optic core 282a. The difference between fiber optical fiber optic cores 282 and 282a is that fiber optic core 282a has an extension 703 that extends forward from the distal end of the body of tube 280a. Core extension 703 may have a roughened surface to ensure that the light that reaches this section of the core will project radially outwardly from this section of the core.

The suction line 702 includes a distal end fitting 704. Fitting 704 is formed from a substantially transparent flexible plastic such as silicon rubber. Fitting 704 has a tube like body 706. The tube body 706 is formed to have proximal bore 708 and a contiguous distal bore 710 that form and axial path between the opposed proximal end distal ends of body 706. The proximal bore 708 is sized to closely receive both the proximal end of suction tube 280a and extension 703 integral with the fiber optic core 282. Fiber optic core extension 703 fits in a closed end cylindrical pocket 711 that is radially spaced outwardly away proximal bore 708. The distal bore 710 of fitting 704 is designed to receive the fitting of a convention suction applicator.

Suction line 702 is used in the same manner in which suction line 680 is used. When the manifold receiver LED 182 to which the line 702 is coupled emits light, the light is transmitted through the proximal end fitting and the fiber optic core 282a. The light is emitted from fiber optic core extension 703 into the fitting body 706. Fitting 706 thus emits light representative of the detected operating state of the waste collection unit 40.

Suction line 720, the fourth alternative suction line, the distal end of which is seen in FIGS. 37A and 37B, includes the previously described suction tube 280. A fitting 722 is disposed over the distal end of tube 280. Fitting 722 has the same basic shape and function as fitting 704. The material forming fitting 722 is opaque. A difference between fitting 704 and 722 is that integral with the body of the fitting 722 is a fiber optic core 724. Fiber optic core 724 extends from the step internal to the fitting 722 against which the distal end of suction tube 280 abuts. The fitting 722 is formed so that as the fiber optic core 724 extends distally the fiber optic core extends outwardly to the outer surface of the body of the fitting. Immediately proximal to the proximal most rib 690 an elongated section of fiber optic core 724 is visible along the outer surface of the body of fitting 722. The exposed surface of fiber optic core 724 may be roughed to ensure that the light that reaches this portion of the core will radiate outwardly.

Suction line 720 is used in the same manner in which suction line 680 is used. When the manifold receiver LED 182 to which the line 720 is coupled emits light, the light is transmitted from the proximal end of fiber optic core 282 into fitting fiber optic core 724. The exposed section of the fiber optic core 724 emits light emits light representative of the detected operating state of the waste collection unit 40.

An alternative version of fiber optic core includes the previously described suction tube 280a. When this version of the invention is manufactured, the fitting 722 is formed around the distal end of the suction tube so that the extension 703 of the fiber optic core 282a functions as the fiber optic core internal to the fitting 722.

FIGS. 38A and 38B illustrate the fifth alternative suction line, suction line 740. Suction line 740 in addition to a proximal fitting, includes suction tube 280 and distal fitting 742. Distal fitting 742 is very close in shape to distal fitting 722. One difference between the two fittings 722 and 742 is that distal fitting 742 is formed from material that, instead of being opaque, is translucent. A further difference between the fittings 722 and 742 is that fitting 742 does not include an embedded fiber optic core.

The distal end of suction tube 280 is disposed in the proximal end bore internal to distal fitting 742. The distal end of fiber optic core 282 abuts the step internal to the fitting 742 that defines the base of the proximal end bore.

At least a portion of the fiber optic core 282 disposed in fitting 742 may be roughed to ensure that the light energy in this portion of the core will radiate into the fitting.

Suction line 740 is used in the same manner in which suction line 680 is used. When the manifold receiver LED 182 to which the line 740 is coupled emits light, the light is transmitted from the proximal end of fiber optic core 282 to the distal end of the fiber optic core 282. The light is emitted into the distal fitting 742. Owing to the translucent nature of the material forming the fitting 742, the fitting takes on the color of the emitted light. Personnel using the suction applicator to which suction line 740 is connected need only have to see the color of distal fitting 742 to determine the characteristic of the operating state of the unit 40 as indicated by the light emitted by the manifold receiver LED 182.

XIII. Alternative Waste Collection Unit and Sixth Alternative Suction Line

Figure 39:
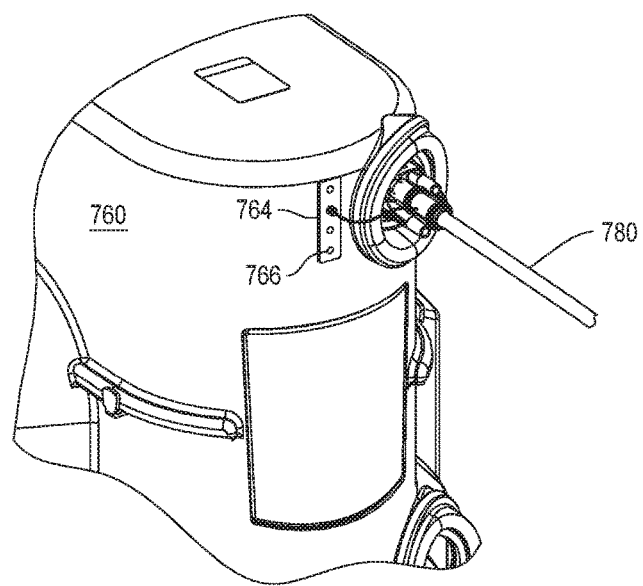
FIG. 39 is a perspective view of an alternative waste collection unit and the proximal end of an alternative suction line of this invention.
Figure 40:
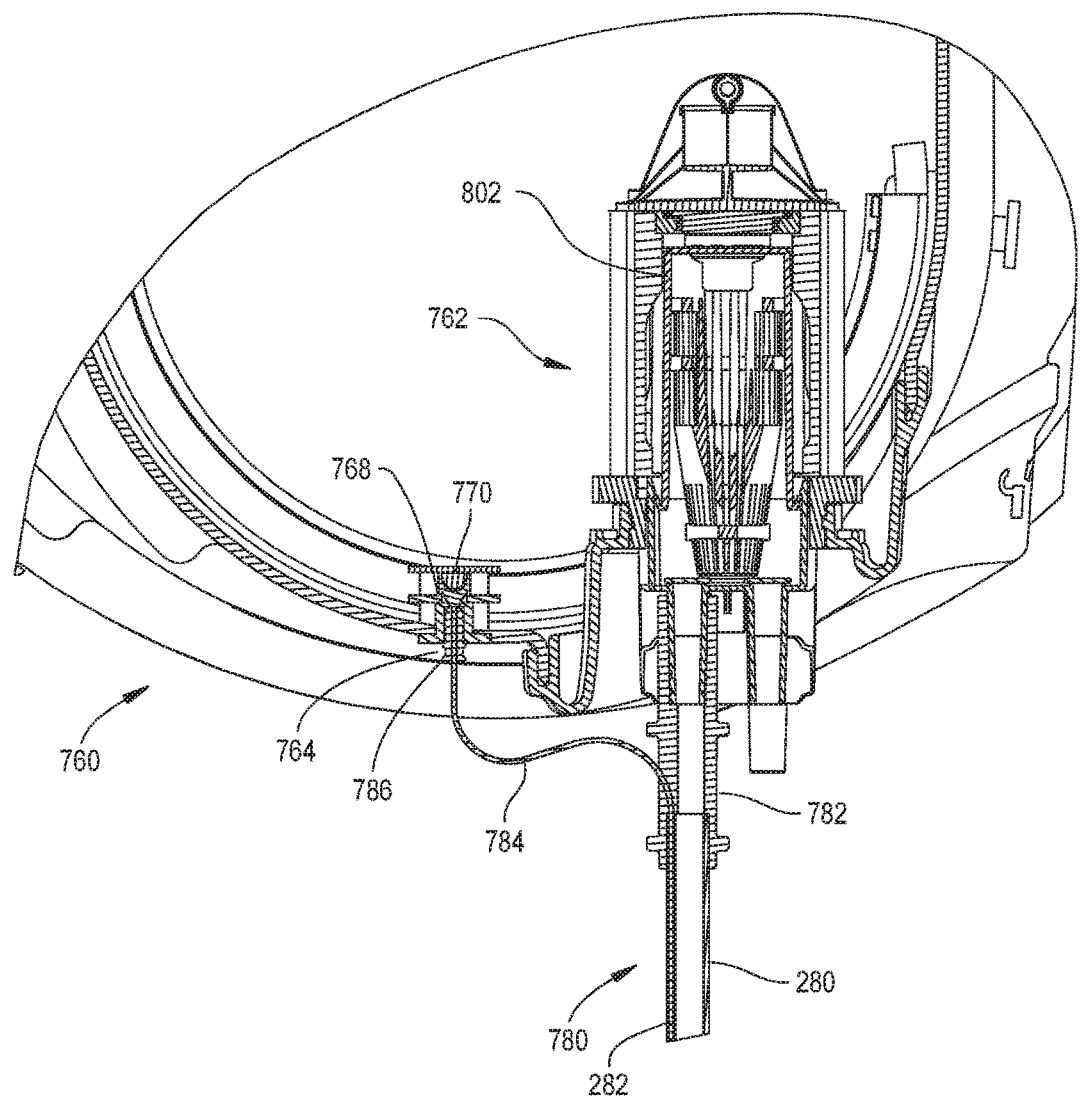
FIG. 40 is a cross sectional view of the waste collection unit and the proximal end of the alternative suction line of this invention.

FIGS. 39 and 40 illustrate an alternative waste collection unit 760 of this invention. A sixth alternative suction line 780 extends from unit 760. Waste collection unit 760, has waste collection container, a vacuum pump for drawing waste into the containers, the sensors, display and processor of the previously described unit 40. Accordingly, these features are not redescribed or illustrated. The waste collection unit 760 also has a conventional manifold receiver 762. Receiver 762 is designed to receive a standard manifold. The receiver 762 does not include any light emitting components. The structure of receiver 762, which is the topic of the previously incorporated by reference U.S. Pat. No. 7,615,037, is therefore not part of the present invention.

Mounted to the chassis of waste collection unit 760 is a light board 764. Light board 764 includes a number of sockets 766. In FIG. 39, four sockets 766 are shown, only one socket is identified. The waste collection unit 760 is constructed so that the sockets 766 are both accessible from outside of the unit and close to the receiver 762.

Four LEDs 770 (one illustrated) are mounted to the light board 764 so as to be spaced inwardly from the inner surface of the light board. LEDs 770 is similar if not identical in structure and function to previously described LEDs 182. The LEDs 770 are mounted to a light bar 768 that is itself mounted to the inner surface of the light board 764. The light bar directs the light emitted by the LEDs 770 into the sockets 766.

The LED 770 is connected to the processor 192 internal to the waste collection unit 760, connection not shown. Processor 192 controls the on/off state of LED 770 as well as which color light is emitted by the LED 770 in a manner similar to that in which it controls LED 182.

Suction line 780 includes a proximal end fitting or cuff 782. Fitting 782 is formed from a flexible material. More specifically, the suction line fitting 782 is formed from material that allows the fitting 782 to be press fit over the fitting integral the manifold 802 to which the fitting is attached. Suction tube 280 extends distally from the distal end of fitting 782. Not illustrated is the cuff or fitting located at the distal end of suction tube 280. One of the previously described fittings or cuffs may be attached to this end of suction tube 280.

The suction line 780 is further designed so that an extension fiber optic core, fiber optic core 784 extends proximally from the proximal end of fiber optic core 282. In some versions of the invention fiber optic cores 282 and 784 are a single fiber optic core. In these versions of the invention, fiber optic core 784 is the most proximal end of this fiber optic core. Fiber optic core 784 extends proximally partially through fitting 782. Fiber optic core 784 also has a section that extends out of fitting 782. A plug 786 is attached to the most proximal end of fiber optic core 784. Plug 786 is dimensioned to seat in any one of the socket 766.

A waste collection system that includes unit 760 and suction line 780 is prepared for use by placing a manifold 802 in receiver 762. Suction line 780 is attached to the unit 760 by first inserting the line fitting 782 over the complimentary manifold fitting. Plug 786 is inserted in one of the sockets 766. If appropriate, the distal end of the suction line is attached to a suction applicator The system is then used in the manner identical to the previously described versions of this invention. Processor 192 receives the signals that represent the operating states of the various parts of the system. Based on at least one of these signals, the processor causes LEDs 770 to emit a specific color of light or emit the light in a specific pattern. The light emitted by the LED is transmitted through fiber optic core 784 into fiber optical fiber optic core 282.

XIV. Display of Alternative Operating State Characteristics

The system of this invention may display information about the operating state or operating characteristics different from what has been described.

For example, the system may display indication regarding how elapsed time of operation of the waste collection unit. This information is useful because this elapsed time of operation of the waste collection unit often has a high correlation to the elapsed time since the start of the procedure or the start of a specific part of the procedure. The practitioner may find this elapsed time useful to determine the overall state of the procedure.

Figure 41:
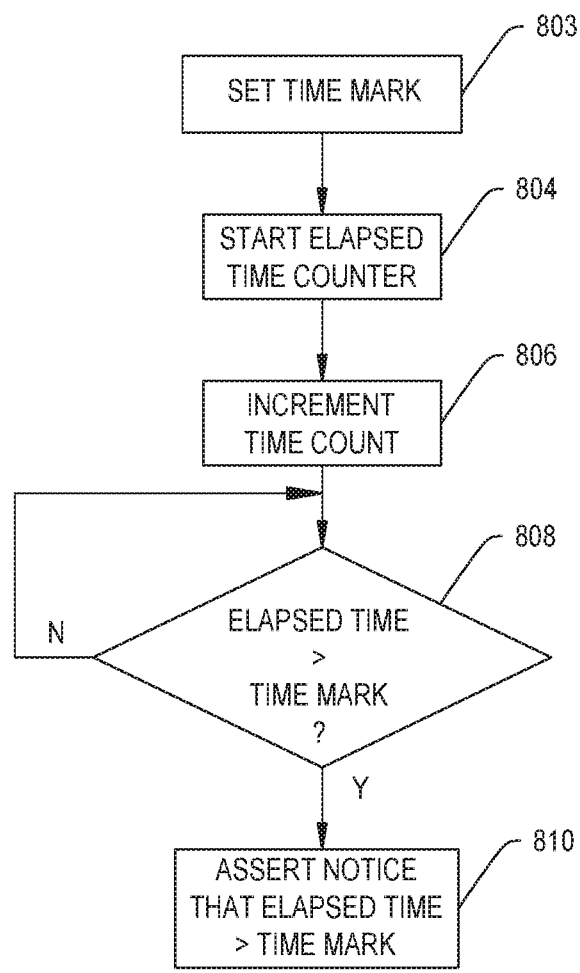
FIG. 41 is a flow chart of how the unit of this invention displays information regarding the elapsed time since the unit was actuated as part of a surgical or medical procedure.

As represented by FIG. 41, the process of monitoring and displaying information regarding the elapse time of operating of the system starts with the setting of time mark, step 803. Step 803 is executed by entering data through display 106. An event occurs which then causes the processor 192 to start an elapsed time count, step 804. This event may be the actual turning on of the suction pump 76 or motor 81 integral with the smoke evacuator assembly 80. Alternatively, the step 804 is triggered by the entry of start timer button presented on display 106.

In response to the execution of step 802, processor 192 initializes and increments a counter of elapsed time, step 806. This counter may be a data field in the memory to which the processor 192 has access. (Neither memory or the counter are illustrated.) In step 808, the processor 192 compares the elapsed time count to the time mark. As long as the elapsed time is less than the time mark time, the processor 192 continues to reexcute steps 806 and 808.

Eventually the elapsed time may exceed the time mark time. Should this event occur, in a step 810, the processor 192 causes a notice to be asserted that the event has occurred. The processor asserts this notice by causing the LEDs 182, 360, 604, 662 or 770 to output light in a specific color or pattern.

Figure 42:
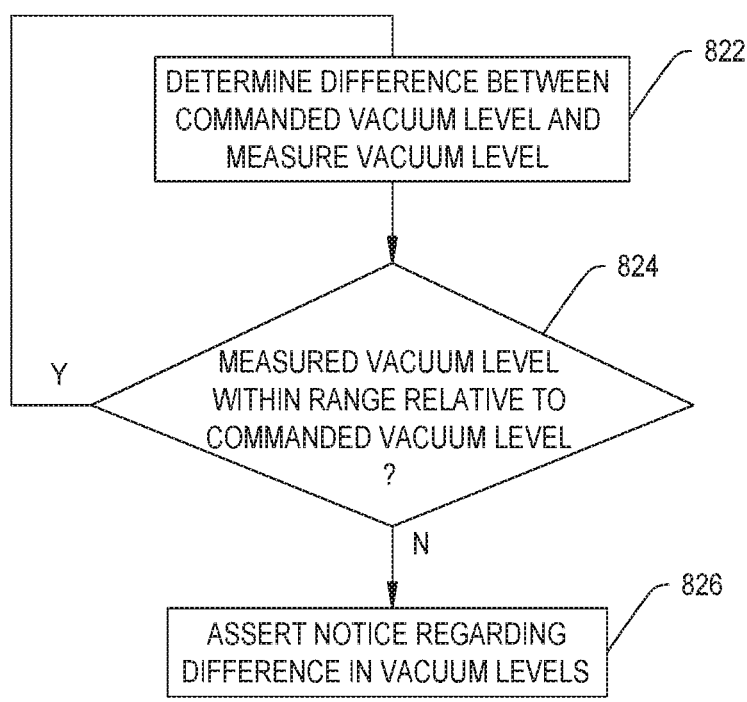
FIG. 42 is a flow chart of how the unit of this invention monitors the one aspect of the performance of the unit and displays information about this aspect of the performance of the unit.

The waste collection unit of this invention may also be set to output light based on signals that indicate whether or not the unit is properly functioning. One such example of how the unit makes this determination is discussed by reference to FIG. 42. As represented by 822 of this Figure, the system may for one or both of the containers 46 and 48 determine the difference between the commanded vacuum level and the measured vacuum level. For container 46 and the suction line attached to the container, step 822 is performed by determining the difference between the vacuum level as commanded by the level entered through the display to the vacuum level as measured by sensor 202.

In a step 824 the processor, based on the difference in vacuum levels, determines whether or not the measured vacuum level is within an acceptably range relative to the commanded vacuum level. If this evaluation tests true, the waste collection unit is considered to be in a state in which the vacuum regulator is properly controlling the level of the vacuum drawn through the suction line. The processor 192 then continues to reexcute steps 822 and 824.

There may be times in which there measured vacuum level significantly varies from the commanded vacuum level. When the waste collection unit is in this state, this may be an indication that there may be a malfunction in one of the components of the unit. Thus, should the unit be in this state, the processor 192, in step 826 causes the appropriate LEDs 182, 604, 662 or 770 to emit light that functions as an indication of regarding the operating state of the unit.

XV. Alternative Versions

The foregoing is directed to specific versions of the invention. Other versions of the invention may have features different from what has been described.

For example, there is no requirement that in all versions of the invention, the unit include both an assembly for collecting liquid and semi-liquid waste and a smoke evacuator. These assemblies may be provided separately from each other.

Likewise, there is no requirement that all versions of this invention be built as part of mobile assemblies. In some versions of the invention, the assembly may be static. Likewise in versions of the invention designed to collect and temporarily store liquid and semi-liquid waste always include two canisters or the means to draw waste simultaneously at two different suction levels. Likewise, there is no requirement that the suction pumps be integral with the waste collection and smoke evacuation units with which the pumps are associated.

The features of the different versions of this invention may be combined. Thus, some versions of this invention may include an assembly that lights at least two of: the manifold receiver; the manifold; and the suction line that extends from the manifold.

Versions of the invention with less than all the disclosed features are possible. For example, in some versions of the invention, a removable manifold may not serve as the interface between the waste collection unit and the suction line. In these versions of the invention there is no manifold receiver. Instead, there may simply be a fitting to which the suction line is attached. In these versions of the invention, the light source, the LED, that emits light for transmission through the suction tube is located in close proximity to this fitting. Here close proximity is understood to mean within 25 cm of the fitting, preferably within 15 cm of the fitting and more preferably within 10 cm of the fitting.

In versions of the invention wherein the waste collection unit includes a manifold receiver, the light source in close proximity to the receiver that emits light about the status of the unit may not be a ring that extends completely circumferentially around the manifold. Instead the light may be a C-shaped member that does only extends arcuately but not completely around the manifold. Alternatively, the light may simply be a bar or a set of dots that are in close proximity to the manifold receiver. Again, close proximity is understood to mean within 25 cm of the manifold fittings, preferably within 15 cm of the fittings and more preferably within 10 cm of the fittings.

In some versions of the invention, the vacuum regulator and display may be less than complex that what has been described. For example, the vacuum regulator may simply be a valve that regulates the vacuum draw the suction pump places on the canister. In these versions of the invention, the display of the commanded suction level may be a pointer on the knob that is rotated to set the valve. In some versions of the invention, the signals output by pressure sensors 202 and 204 may not be forwarded only to the processor. In some versions of the invention the signals or digitized may be forwarded to a display circuit. The display circuit, based on these signals generates the images 112 of measured suction level that are presented on the display 108. Alternatively, the display may be the face of gauge that is part of the sensor assembly.

It should similarly be clear that there is no requirement that all versions of the invention include the described suction applicators and smoke pens specifically designed for use as part of the system. This invention can be used with conventional smoke applicators or smoke pens. In these assemblies of the invention, the medical personnel determine the operating state of the waste collection unit by viewing the color of the light emitted by the fiber optic core embedded in the suction line. In the smoke evacuators of these versions of the invention, the medical personnel determine the operating state of the smoke evacuator by viewing the light emitted by the fiber optic core embedded in the smoke line.

Likewise, there is no reason that the suction lines of this invention always be attached to a suction applicator. The free distal end of the suction line can function as the device through which is drawn. Similarly, the free end of the smoke line can function as the device through which smoke is evacuated.

Alternative constructions of the various components of this invention are likewise possible. For instance in versions of the invention wherein there is a manifold receiver, the receiver may not include a valve for opening/closing the connection to the canister 46 or 48. If a valve is present, the valve may have a structure different from what has been described. Two potential alternative valves are flapper valve and duck-billed valves.

Some manifold receivers of this invention are constructed so that include light tubes are constructed so that the light tube and lock ring are a single piece component.

There is no requirement that in all versions of the invention the component through which light is piped through the suction line or smoke line be a fiber optic core embedded in the line. In some versions of the invention the tube forming the suction line or the smoke line may itself be formed from material through which light can be transmitted. Generally, though it is believed preferable for the lumen internal to a suction line or a smoke line to be visible along the length of the line. This allows the personnel to inspect the line during the procedure to determine the contents of the line and/or whether or not a clog is present in the line.

In versions of the invention wherein a fiber optic core is embedded in the suction tube or smoke tube, portions of the fiber optic core may extend out of the ends of the tube which the fiber optic core is embedded. These proximal or distal extensions of the fiber optic core function as the fiber optic core that is embedded in the proximal or distal fittings attached to the line. Thus in these versions of the invention, the fitting is molded over the exposed end of the fiber optic core. Either a suction line or a smoke line of this invention may include a single fiber optic core that extends the whole length of the tube, from within the proximal fitting, through the tube portion of the line and into the distal fitting.

Similarly, the manifold to which the suction lines are attached may have geometric features different from what has been described. For example some manifolds may not be generally cylindrical in shape. Other manifolds may have less than or more than the four fittings of the illustrated manifolds.

Further, it should be recognized that the status information displayed by the selectively illumination of the manifold receiver, the manifold, the suction line or the smoke line may vary from what has been described. For example, some waste collection systems of this invention include features able to tell is certain components such as the manifolds or suction lines are suitable for use with the system. One such system is disclosed in the Applicant's PCT Pub. No. WO 2007/103842 A2, (PCT App. No. PCT/US2007/063253) the contents of which is explicitly incorporated herein by reference. If the processor determines that a component is not to be used with the system, the processor will cause the LEDs to emit a color of light or a pattern of light understood by the medical personnel to represent this fact. Likewise, in some versions of the invention, the light emitted for transmission of the suction line does not vary as a function of the measured suction. Instead, in step 458, processor 192 asserts signals that cause the LEDs 182 to emit a color of light or a pattern of light as a function of the level of the vacuum that has been set for the line, the commanded vacuum draw.

It should also be understood that the versions of the fittings 680, 702, 720 and 740 depicted as part of the alternative suction line may be incorporated into alternative smoke lines of this invention. These alternative smoke lines would then be used with convention smoke pens that do not include components capable of emitting or transmitting lights. Likewise, a smoke filter may include a version of the light board 764 of FIGS. 39 and 40. In this version of the invention, the proximal end of the smoke line may be like the proximal end of suction line 780.

It is likewise within the spirit and scope of the invention so as to provide an opaque sleeve over the fiber optic core embedded in a suction line or a smoke line of this invention. This sleeve is not present within the distal section of the suction tube or smoke tube through which the sleeve and underlying core extend. The sleeve prevents the light that goes through the fiber optic core with interfering with the view of the material flowing through the smoke or suction line. Since the sleeve is not present adjacent the distal suction of the tube, the light radiated from the sleeve-free section of the core does provide an indication of the operating condition of the device to which the line is attached.

Different combinations of the features of this invention are also possible. Thus, some versions of the invention may include plural separate sets of lights associated with a single canister. For example in one version of the invention a first set of lights may source light to the suction line 250 and attached suction applicator. A second set of lights sources light to a translucent member adjacent where the suction line is attached to the canister. In these versions of the invention, the light or light pattern emitted by the first set of lights may vary as a function of the commanded or measured suction draw through the suction line. The processor causes the second set of lights to emit the light or a light pattern as a function of the measured volume of waste collected in the canister.

Figure 43:
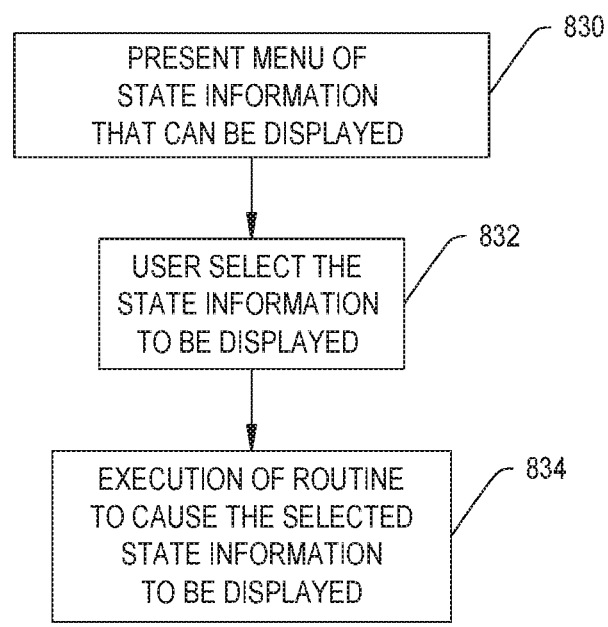
FIG. 43 is a flow diagram of how the unit of this invention, in response to a command causes light to be displayed that is function of the state of interest of the personnel using the unit.

It should similarly be appreciated that the unit of this invention could be configured to emit light from a particular light emitting device as a function of a variable selected by the practitioner using the unit. Thus, when the unit of this invention is initially actuated, prior to the execution of step 452, processor 192 presents on the display 106 a menu of possible state information the practitioner can have displayed by the lights integral with the unit 40, step 830 of FIG. 43. Step 832 represents the practitioner indicating the type of information he/she wants displayed. Step 834 represents the execution of the routine by the processor that causes the requested information to be displayed. For example, the practitioner may want to have the light change as a function of the measured vacuum level through the suction line 250. If this is the information that is requested, processor 192 essentially executes the routine of FIGS. 24A and 24B. Alternatively, the practitioner may want the emitted light to be a function of the commanded vacuum draw. This is so the practitioner can know the suction the applicator will draw prior to applying the suction to a site. If this is the information the practitioner prefers to receive, processor executes the version of the routine of FIGS. 24A and 24B wherein, in step 458 the light is emitted as a function of the commanded level of vacuum draw. The unit may also be set to selectively emit light that functions as an indicia the unit is in another operating state.

In some versions of the invention a single differential pressure sensor may replace the two sensors 372 and 382 found in the smoke filter 320.

Thus it is an object of the appended claims to cover all such modifications and variations that come within the true spirit and scope of this invention.

What is claimed is:

1. A waste collection unit, said waste collection unit including:
   at least one canister configured to be arranged in fluid communication with a suction line and defining a volume for receiving medical/surgical waste;
   a manifold receiver comprising an opening in fluid communication with said at least one canister and configured to receive a manifold;
   a vacuum regulating assembly for regulating a vacuum drawn on said at least one canister so as to cause a vacuum draw on the suction line connected to said at least one canister;
   a display panel on which information is presented regarding at least one of a measured level of vacuum draw on said at least one canister and a commanded level of the vacuum draw;
   a light assembly separate from said display panel and positioned on said waste collection unit near said manifold receiver such that said light assembly is located near the manifold when the manifold is received within said opening and the suction line when the suction line is in communication with said at least one canister, wherein said light assembly is configured to selectively emit light of different colors or different patterns; and
   a processor which receives signals regarding an operating state of said waste collection unit based on said at least one of the measured level of the vacuum draw and the commanded level of the vacuum draw, wherein said processor is connected to said light assembly for regulating the light emitted by said light assembly based on the operating state of said waste collection unit.

2. The waste collection unit of claim 1, further comprising:
   a sensor connected to said at least one canister for measuring the level of vacuum draw on said canister,
   wherein said processor is configured to regulate a specific color of light emitted by said light assembly or a specific pattern of light emitted by said light assembly as a function of either the measured level of the vacuum draw on said at least one canister or the commanded level of the vacuum draw.

3. The waste collection unit of claim 1, wherein:
   said display panel is configured to present text or images representative of the commanded level of the vacuum draw; and
   said processor is configured to regulate a specific color of light emitted by said light assembly or a specific pattern of light emitted by said light assembly as a function of the commanded level of the vacuum draw.

4. The waste collection unit of claim 1, further comprising a manifold configured to be removably disposed in said opening of said manifold receiver and said manifold comprising at least one fitting dimensioned to receive the suction line.

5. The waste collection unit of claim 4, wherein said light assembly is further defined as a light ring configured to extend circumferentially around said manifold when said manifold is removably disposed in the opening of said manifold receiver.

6. The waste collection unit of claim 1, further comprising a suction pump with said vacuum regulator configured to selectively connect said at least one canister to said suction pump.

7. The waste collection unit of claim 6, wherein said vacuum regulator is configured to control the level of the vacuum drawn on said at least one canister and selectively establish fluid communication between said at least one canister and said suction pump, the ambient environment, or neither said suction pump nor the ambient environment.

8. The waste collection unit of claim 1, further comprising a mobile base, wherein said at least one canister, said display panel, said processor, and said light assembly are mounted to said mobile base.

9. The waste collection unit of claim 1, wherein said light assembly includes at least one LED capable of emitting the different colors of the light.

10. A waste collection unit, said waste collection unit including:
- at least one canister for receiving medical/surgical waste;
- a manifold receiver in fluid communication with said at least one canister and comprising a vacuum opening and at least one light bore separate from said vacuum opening;
- a light assembly comprising a light in communication with said at least one light bore;
- a manifold configured to be removably received within said vacuum opening of said manifold receiver and comprising a head comprising at least one fitting dimensioned to receive a suction line, said head further comprising a socket extending through said head and positioned adjacent said at least one fitting such that, when said manifold is positioned within said opening of said manifold receiver and the suction line is coupled to said at least one fitting, said socket is in registration with said at least one light bore of said manifold receiver and a fiber optic core integral with the suction line is in registration with said socket;
- a vacuum regulating assembly for regulating a vacuum drawn on said at least one canister so as to cause a vacuum draw on the suction line connected to said at least one canister through said fitting, said vacuum regulating assembly including a manually actuated control member over which a commanded level of the vacuum draw can be entered.

11. A waste collection unit, said waste collection unit including:
- at least one canister for receiving medical/surgical waste;
- a manifold receiver connected to said at least one canister, said manifold receiver having an opening for removably receiving a manifold to define a fluid communication path between the manifold and said at least one canister;
- a vacuum regulating assembly for regulating a vacuum drawn on said at least one canister so as to cause a vacuum draw on the manifold in said fluid communication path;
- a display panel on which information is presented regarding at least one of a measured level of vacuum draw on said at least one canister and a commanded level of the vacuum draw;
- a pressure sensor associated with said at least one canister and configured to generate vacuum level signals indicative of said measured level of the vacuum draw;
- a light assembly separate from said display panel and configured to selectively emit light of different colors or different patterns; and
- a processor connected to said pressure sensor and configured to receive the vacuum level signals, and connected to said light assembly for regulating the color of the light emitted by said light assembly,
- wherein said processor is configured to control said light assembly based on the vacuum level signals received from said pressure sensor to emit a first color or pattern of the light based on a first measured or commanded level of the vacuum draw, a second color or pattern of the light, different than said first color or pattern of the light, based on a second measured or commanded level of the vacuum draw being greater than said first measured or commanded level of the vacuum draw.

12. The waste collection unit of claim 11, wherein said display panel is configured to present text or images representative of the commanded level of the vacuum draw.

13. The waste collection unit of claim 11, wherein said light assembly includes at least one LED capable of emitting the different colors of the light.

14. The waste collection unit of claim 11, wherein said processor is further configured to control said light assembly to emit a third color or pattern of the light, different than said first and second colors or patterns of the light, based on a third measured or commanded level of the vacuum draw being greater than the first and second measured or commanded levels of the vacuum draw.

15. The waste collection unit of claim 14, wherein said first color is green and said first measured or commanded level is a low suction level, said second color is yellow and said second measured or command level is a medium suction level, and said third color is orange and said third measured or commanded level is a high suction level.

* * * * *